US007319021B2

(12) United States Patent
Engel et al.

(10) Patent No.: US 7,319,021 B2
(45) Date of Patent: Jan. 15, 2008

(54) CELL LYSIS COMPOSITION, METHODS OF USE, APPARATUS AND KIT

(75) Inventors: Laurie Engel, DeForest, WI (US);
John W. Schultz, Verona, WI (US);
Tonny M. Johnson, Madison, WI (US);
Kristopher Zimmerman, Madison, WI (US); Laura L. Bozek, Madison, WI (US); Judith N. Stevens, Oregon, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 10/673,054

(22) Filed: Sep. 26, 2003

(65) Prior Publication Data

US 2004/0101947 A1 May 27, 2004

Related U.S. Application Data

(60) Provisional application No. 60/422,931, filed on Nov. 1, 2002.

(51) Int. Cl.
*C12P 21/06* (2006.01)
*C12P 21/04* (2006.01)
*A23J 1/00* (2006.01)

(52) U.S. Cl. ..................... 435/69.1; 435/71.1; 530/412
(58) Field of Classification Search ............... 435/69.1, 435/71.1; 530/412
See application file for complete search history.

(56) References Cited

U.S. PATENT DOCUMENTS

| | | | | |
|---|---|---|---|---|
| 4,797,474 | A | 1/1989 | Patroni et al. ............... | 530/351 |
| 4,992,531 | A | 2/1991 | Patroni et al. ............... | 530/351 |
| 5,489,676 | A | 2/1996 | Elsbach et al. ............. | 536/22.1 |
| 5,593,866 | A | 1/1997 | Hancock et al. ........... | 435/69.7 |
| 5,760,189 | A | 6/1998 | Vicik et al. .................. | 530/412 |
| 5,973,137 | A | 10/1999 | Heath ......................... | 536/25.4 |
| 5,981,235 | A | 11/1999 | Shultz et al. ............... | 435/91.1 |
| 6,174,704 | B1* | 1/2001 | Chu et al. ................... | 435/69.1 |
| 6,210,915 | B1 | 4/2001 | Shay et al. ..................... | 435/15 |
| 6,242,235 | B1* | 6/2001 | Shultz et al. ............... | 435/194 |
| 2001/0034066 | A1 | 10/2001 | Alam .......................... | 436/86 |
| 2002/0012982 | A1 | 1/2002 | Blakesley et al. ........... | 435/183 |
| 2003/0054435 | A1 | 3/2003 | Grabski ...................... | 435/68.1 |

FOREIGN PATENT DOCUMENTS

| | | |
|---|---|---|
| EP | 0 173 937 A2 | 3/1986 |
| EP | 0 222 725 B1 | 3/1992 |
| EP | 0 671 473 A1 | 9/1995 |
| WO | WO 01/00668 A1 | 1/2001 |
| WO | WO 01/75147 A1 | 10/2001 |
| WO | WO 02/06456 A1 | 1/2002 |
| WO | WO 02/057478 A1 | 7/2002 |

OTHER PUBLICATIONS

Product Description for n-Octyl-b-D-thioglucoside, http://www.dojindo.com/newprod/1/cell-m/detergen/8sglu.html, 2003.
Novagen, Inc. Product Description for BugBuster® Extraction Reagent, 2002.
Novagen, Inc. Product Description for His⊖Bind® Kits, 2002.
Pierce Product Description and Instructions for B-PER® Bacterial Protein Extraction Reagent, 2001.
Sigma-Aldrich Co. Product Description for Octyl-b-D-1-thioglucopyranoside, http://www.sigmaaldrich.com/cgi-bin/hsrun/Distributed/Hahtshop/HahtShop.htx;start=frm, 2003.
Tomah Products, Inc. Product Description For Ethoxylated Amines, 1998.
Fox, Charles, "Rationale For the Selection of Emulsifying Agents", *Cosmetics & Toiletries*, vol. 101, 1986, pp. 25-44.
Graciaa, A., et al., "A Study of the Required Hydrophile-Lipophile Balance for Emulsification", *Landmuir*, vol. 5, 1989, pp. 1315-1318.
Griffin, William C., "Calculation of HLB Values of Non-Ionic Surfactants", *Journal of the Society of Cosmetic Chemists*, vol. 5, 1954, pp. 249-256.
Griffin, William C., "Classification of Surface-Active Agents by HLB", *Journal of the Society of Cosmetic Chemists*, vol. 1, 1949, pp. 311-326.
Mörbe, et al., "Release of Miniantibodies from E. coli Cells into the Supernatant at Low and High Cell Densities," *Microbiological Research*, vol. 152, 1997, pp. 385-394.
Berg B. Hofsten AV., "The Ultrastructure of the Cellulolytic Bacterium Cellvibrio Fulvus.", *Can. J. Microbiol.*, Mar. 1975, vol. 21, No. 3, p. 386-391. (Abstract Only).
Hancock, R.E.W., "Alterations In Outer Membrane Permeability", *Ann. Rev. Microbiol.*, 1984, vol. 38, p. 237-264.
Lin, Jung-Hsin et al., "Stability of a Melittin Pore in a Lipid Bilayer: A Molecular Dynamics Study", *Biophysical Journal*, Apr. 2000, vol. 78, p. 1714-1724.
Grabski, et al., "Automated Methods for Solubility Screening and Recombinant Protein Purification", *American Biotechnology Laboratory*, pp. 34, 36 and 38 (Aug. 2003).
Grabski et al., "Automated purification of recombinant proteins in a 96-well format with RoboPop™ Kits and robotic sample processing", *Innovations Newsletter*, No. 14, pp. 2-5 (Jul. 2002).

(Continued)

*Primary Examiner*—Jeffrey Siew
*Assistant Examiner*—Vanessa L. Ford
(74) *Attorney, Agent, or Firm*—McDonnell, Boehnen, Hulbert & Berghoff, LLP

(57) ABSTRACT

Cell lysis compositions, methods for extracting and isolating proteins and peptides from a host cells using the compositions, kits and apparatus for extracting and isolating protein and peptide molecules from host cells and for detecting for the presence of a protein or peptide. The composition allows for the extraction and isolation of proteins and peptides from host cells without the need for mechanical disruption and with or without isolation of the cells from cell medium. The composition includes at least one surfactant having a hydrophobic-lipophilic balance value in the range from about 11 to about 16; and at least one cell membrane altering compound.

1 Claim, 13 Drawing Sheets

OTHER PUBLICATIONS

Grabski et al., "Automated solubility screening of recombinant proteins in a 96-well format", *Innovations Newsletter*, No. 16, pp. 11-13 (Mar. 2003).

Grabski et al., "BugBuster™ and Benzonase®: The clear solutions to simple, efficient extraction of *E. coli* proteins", *Innovations Newsletter*, No. 10, pp. 17-19.

Grabski et al., "Extraction and purification of proteins from *E. coli* without harvesting cells", *Innovations Newsletter*, No. 13, pp. 1-4 (Nov. 2001).

Loomis et al., "Centrifugation-free protein extraction and purification from total cultures of baculovirus-infected insect cells", *Innovations Newsletter*, No. 15, pp. 16-19 (Nov. 2002).

Mehler et al., "Robotic solubility screening and purification of fusion proteins", *Innovations Newsletter*, No. 18, pp. 20-22.

Saito et al., "Characteristics of N-octyl β-D-thioglucopyranoside, a new non-ionic detergent useful for membrane biochemistry," *Biochem. J.*, 1984, vol. 22, pp. 829-832.

\* cited by examiner

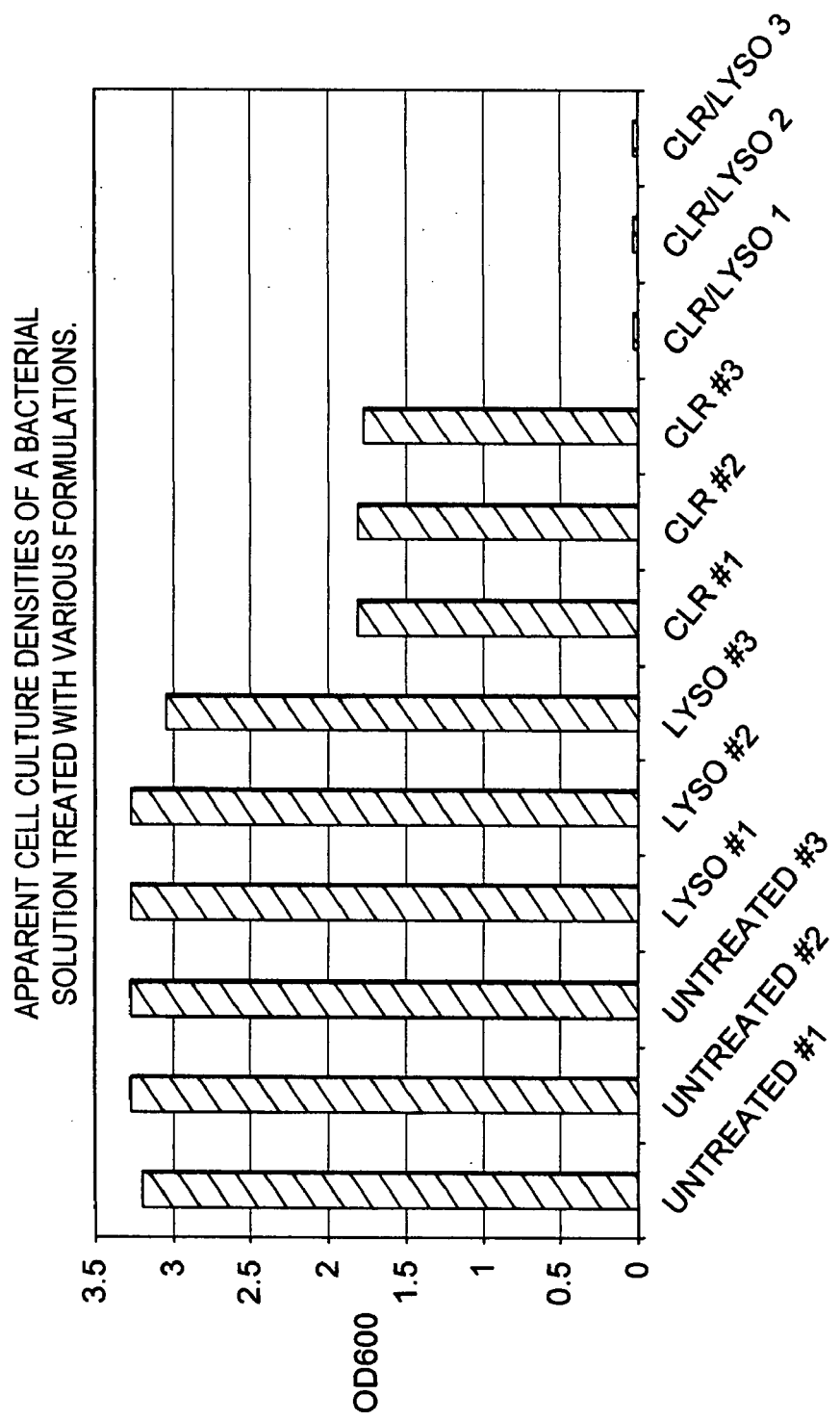

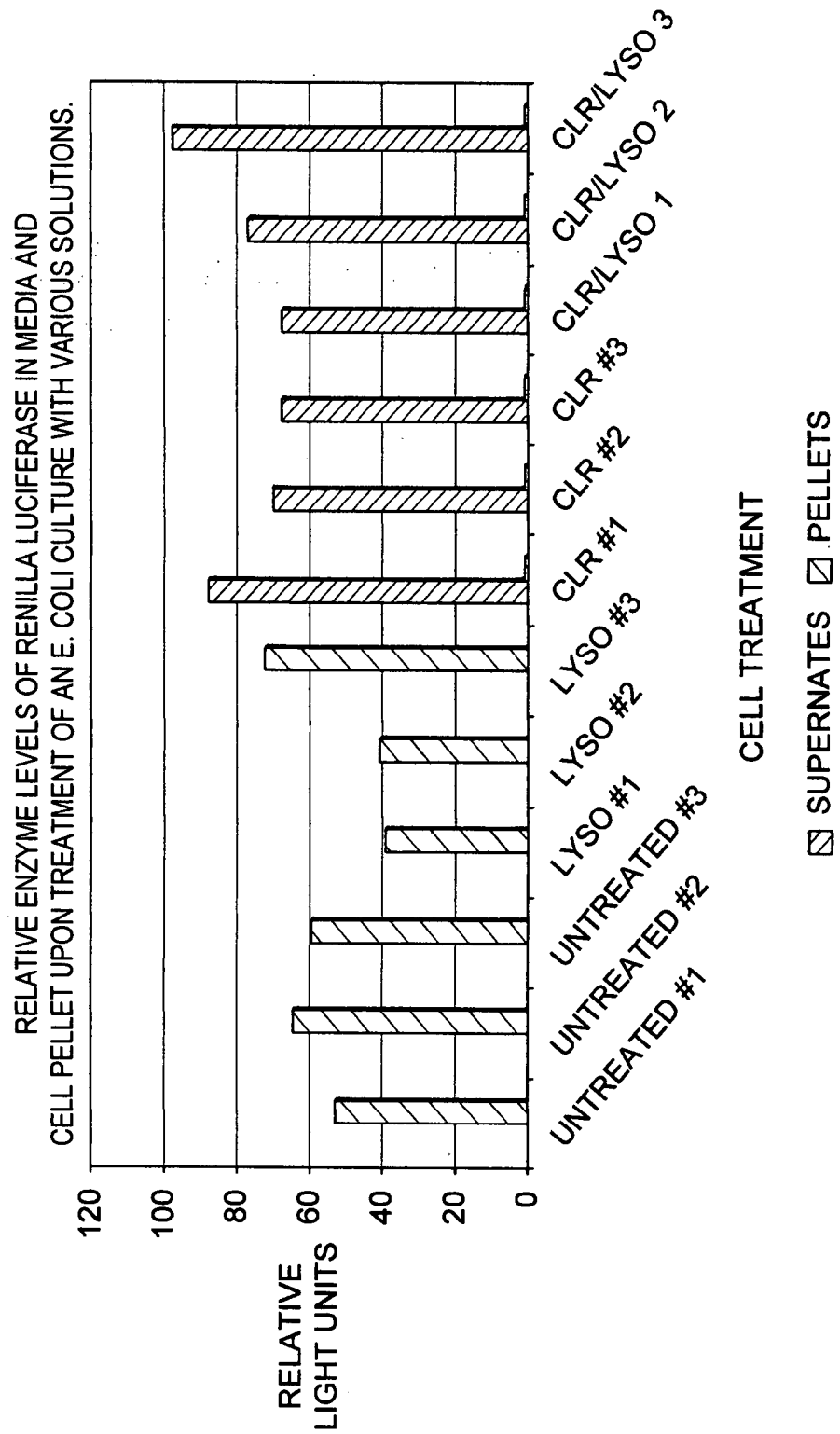

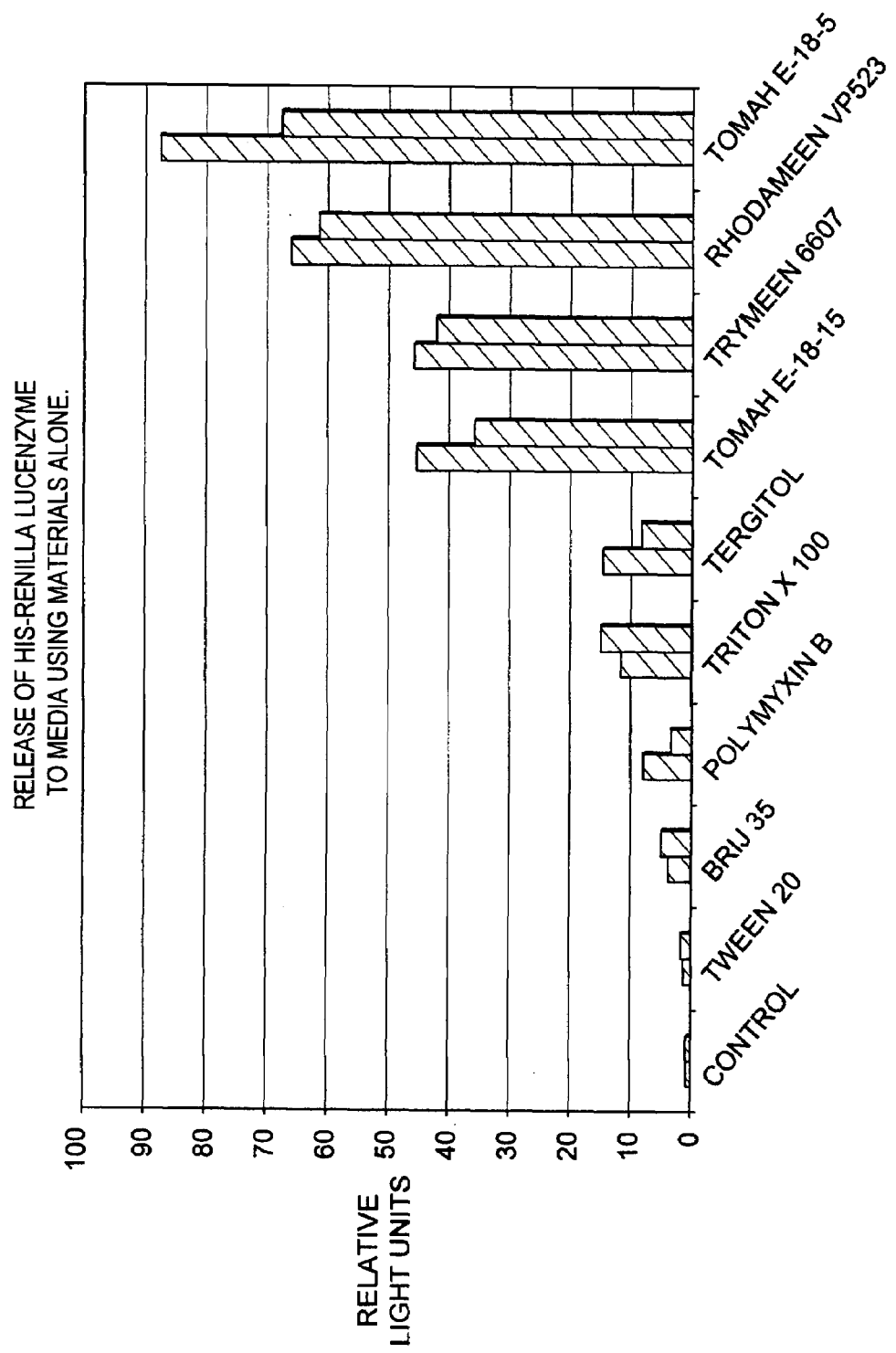

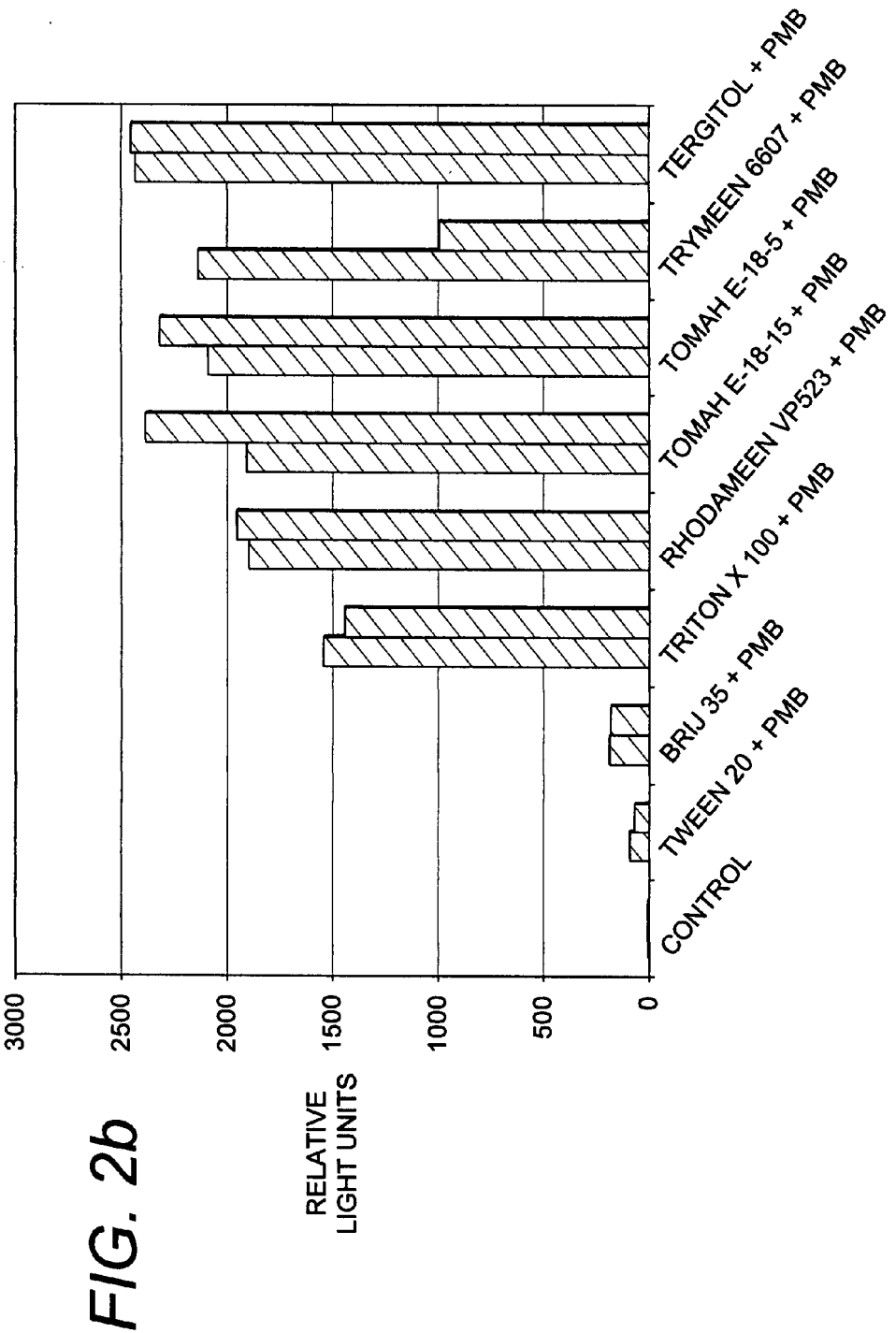

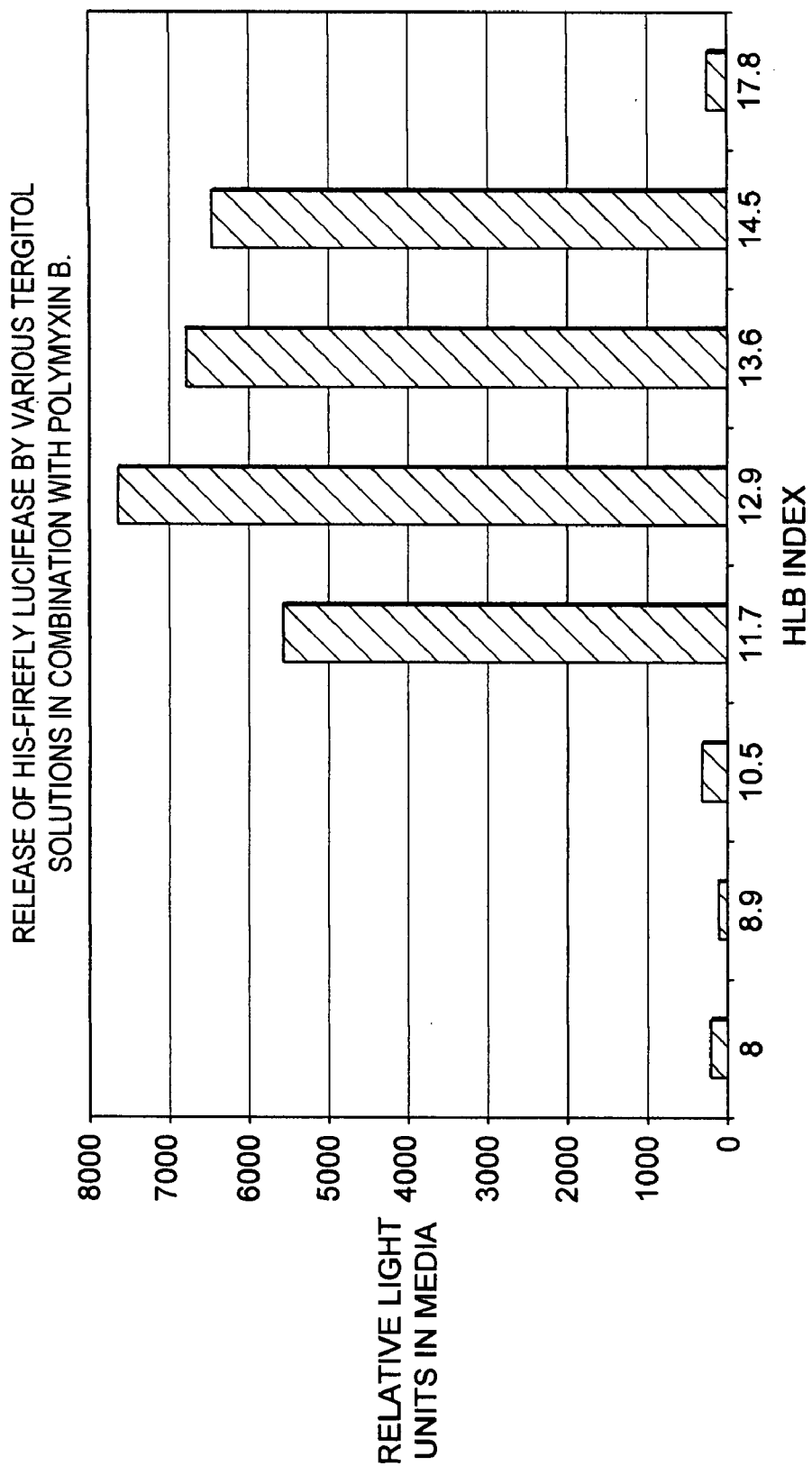

FIG. 9
HIGH THROUGHPUT PURIFICATION OF PROTEINS USING
1 X LYSIS REAGENT IN DIFFERENT ROBOTIC PLATFORMS.
A1 - H8: CORRESPONDING WELLS IN A 96-WELL PLATE.
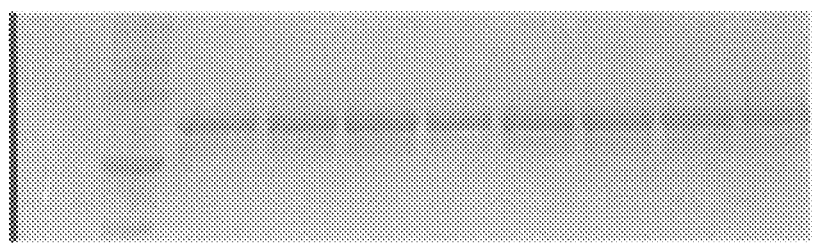
BECKMAN FX
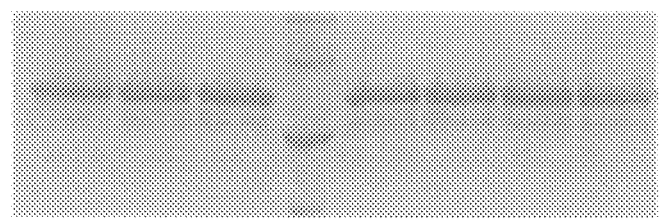
BECKMAN BIOMEK 2000
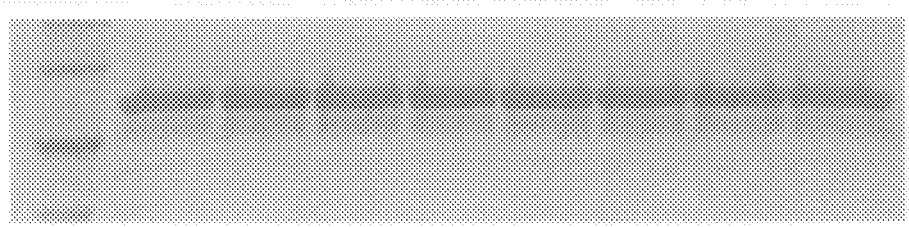
TECAN GENESIS RSP

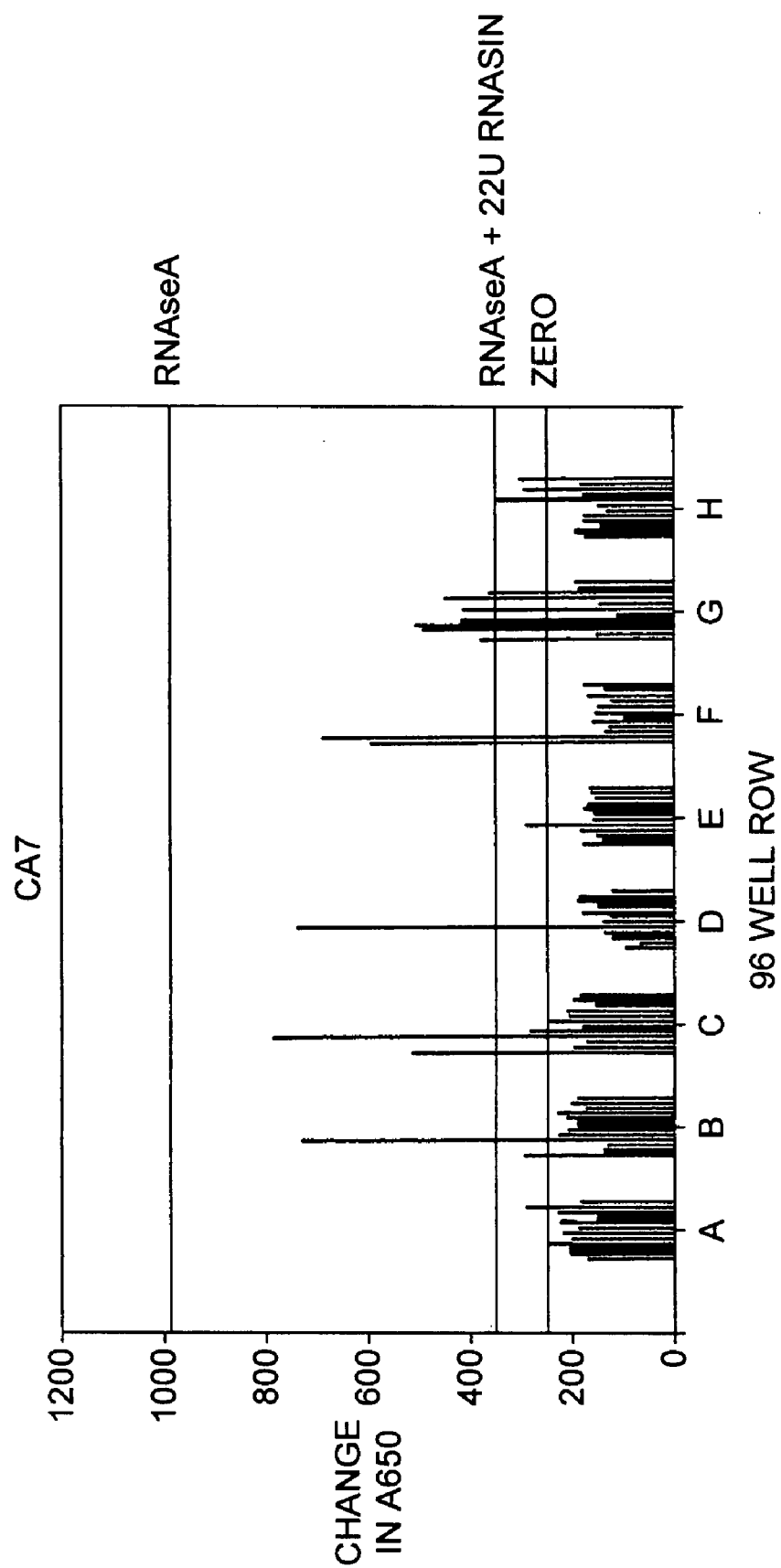

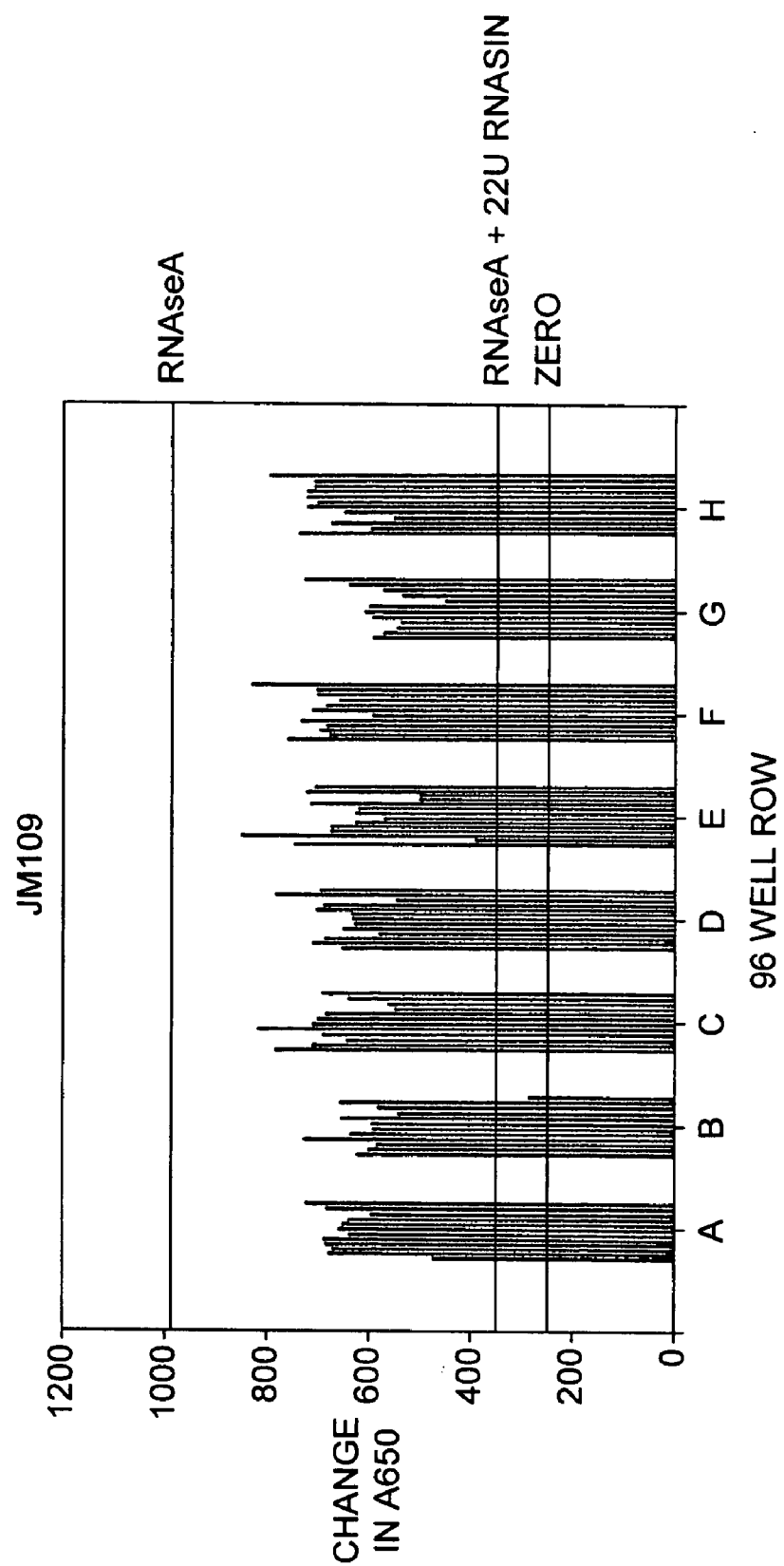

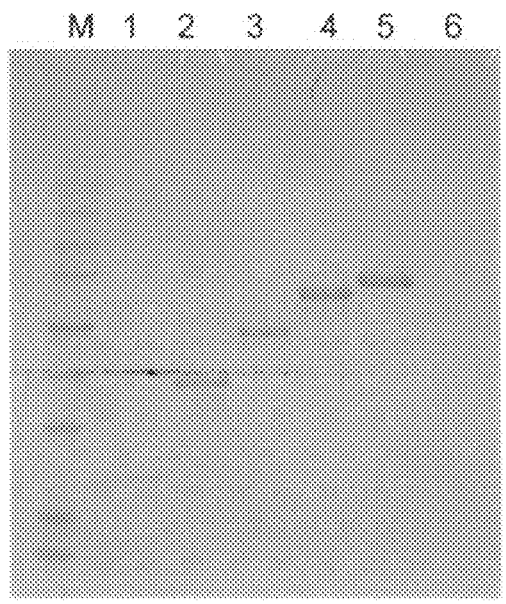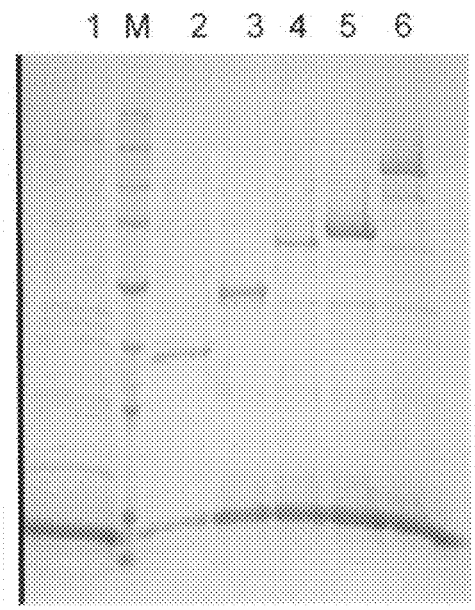
FIG. 12A  –LYSOZYME
FIG. 12B  +LYSOZYME

CELL LYSIS COMPOSITION, METHODS OF USE, APPARATUS AND KIT

CROSS-REFERENCE

This application claims the benefit of U.S. provisional application No. 60/422,931, filed Nov. 1, 2002, which is incorporated by reference in its entirety.

FIELD OF THE INVENTION

The present invention relates to a cell lysis composition, methods for extracting and purifying proteins, apparatus and kit for extracting target proteins from host cells including cell media and cell pellets. In particular, the present invention relates to a composition for extracting proteins from host cells without the need for mechanical disruption.

BACKGROUND OF THE INVENTION

Recombinant DNA technology provides a valuable means of synthesizing large amounts of desirable eukaryotic proteins such as mammalian hormones, interferons, and enzymes. While organisms can be readily manipulated in order to produce the desired protein, the host organism does not normally secrete the protein product into the culture medium. Thus lysis of the organisms, e.g., bacteria, followed by isolation of the desired protein is usually necessary.

Generally, the first step in the purification of native and recombinant proteins entails lysis of the cells producing the proteins, resulting in liberation of the cellular components. Classic physical methods for cell lysis include sonication and the use of a French Pressure Cell, often in combination with a chemical or enzyme agent to aid in lysis. Lysis by physical methods produces membrane fragments and small DNA molecules caused by shearing of the chromosomal DNA, either of which can interfere with subsequent separation and/or analysis of the desired proteins. Removal of these contaminants requires additional costly and time-consuming purification steps, including DNA digestion.

Classic protein purification methods include precipitation (e.g. PEI, PEG, and ammonium sulfate), filtration, preparative electrophoresis and the like. These methods are often performed on bacterial lysates or partially purified preparations of protein. Additional methods based on chromatography include, but are not limited to, ion-exchange chromatography, size-exclusion chromatography, hydrophobic interaction chromatography, and affinity chromatography. Any and all of these methods are dependent on an efficient lysis procedure in order to insure adequate yield.

While methods exist in the art for lysis of cells, there exists a need in the art for a rapid method which employs a gentle cell lysis and avoids mechanical disruption; separation of the protein and peptide of interest from contaminating cellular debris, including DNA and membrane fragments; and additional purification methods into one or a few procedures. The present invention provides such compositions, methods and kits.

SUMMARY OF THE INVENTION

The present invention relates generally to compositions, methods and kits for use in extracting and isolating protein and peptide molecules. More specifically, the invention relates to such compositions, methods and kits that are useful in the extraction and isolation of protein and peptide molecules from host cells (e.g., bacterial cells, animal cells, fungal cells, yeast cells or plant cells) via lysis and one or more additional isolation procedures. In particular, the invention relates to compositions, methods and kits wherein desired protein and peptide molecules are extracted and isolated from a host cell in one or a few procedures using a cell lysis composition for lysing cells and releasing proteins from cells and a substrate for binding protein and peptide molecules.

The invention provides a composition for lysing host cells. The composition comprises: (a) at least one surfactant having a hydrophobic-lipophilic balance value in the range of about 11 to about 16; and (b) at least one cell membrane altering compound. The surfactant may be selected from the group consisting of non-ionic surfactants, cationic surfactants, and mixtures thereof and is present in the composition in an amount ranging from about 0.001 to about 10% (w/w) of the composition. The cell membrane altering compound may be an antibiotic such as polymyxin B sulfate or vancomycin or a mixture of polymyxin B1 and polymyxin B2. The composition may include a buffer in an amount sufficient to maintain a pH of the composition at a range from about 6.5 to about 9.0. If desired, the composition may include other components such as a defoamer or lysozyme. The composition may be in solid form for reconstitution with water, an aqueous solution, or an aqueous concentrate.

The invention also provides a method for recovering proteins from host cells such as bacterial, yeast, insect or plant cells. The method comprises the steps of: providing a source of cells having a desired protein; providing a composition comprising at least one surfactant having a hydrophobic-lipophilic balance value in the range from about 11 to about 16 and at least one cell membrane altering compound; and contacting the cells with the composition in sufficient amount to effect lysis of the cell and subsequent release of the protein. The cells may be in cell culture or in pellet form. In one aspect of the invention, the method further comprises the step of separating the released protein. The released protein may be separated by contacting the protein with a substrate that binds the released protein. Representative examples of substrate include any suitable chromatographic medium such as a magnetic or non-magnetic resin.

The invention also provides a method for isolating protein in purified form. The method comprises the steps of: providing a source of cells having a desired protein; providing a composition comprising at least one surfactant having a hydrophobic-lipophilic balance value in the range from about 11 to about 16 and at least one cell membrane altering compound; providing a substrate for binding the protein; contacting the cells with the composition in sufficient amount to lyse the cells and release the protein; contacting the released protein with the substrate under conditions effective for binding the released protein with the substrate; washing the protein bound to the substrate; and recovering the protein bound to the substrate.

The invention also provides an apparatus for extracting and isolating protein. The apparatus comprises: a housing capable of receiving a sample having a protein or peptide to be extracted and isolated; a composition comprising at least one surfactant having a hydrophobic-lipophilic balance value in the range from about 11 to about 16; and at least one cell membrane altering compound; and a substrate that binds proteins. Suitable housing includes a container, a column, or a multi-well plate. The substrate includes a chromatographic resin or membrane. In one aspect of this invention, the apparatus is included in a kit for isolating a protein.

The invention also provides kits for recovering proteins from host cells, for detecting the presence of a protein in a sample, and for preparing cell lysates. The kit comprises: at least one surfactant having a hydrophobic-lipophilic balance value in the range from about 11 to about 16; at least one cell membrane altering compound; and directions for using the kit. The kit may include a composition comprising at least one surfactant having a hydrophobic-lipophilic balance value in the range from about 11 to about 16; and at least one cell membrane altering compound. If desired, the composition is an aqueous solution. The solution may be in the form of a concentrate. The kit may optionally include other components which may be included as part of or separate from the composition such as buffer salts and lysozyme. The kit may also include one or more washing buffers, elution buffers, substrate for binding proteins.

In one embodiment of the invention, a composition is provided which comprises:

(a) at least one surfactant having a hydrophobic-lipophilic balance value in the range from about 11 to about 16; and
(b) at least one cell membrane altering compound.

In one aspect of this embodiment of the invention, the surfactant is selected from the group consisting of non-ionic surfactants, cationic surfactants, and mixtures thereof. The surfactant is preferably present in the composition in an amount ranging from about 0.001 to about 10% (w/v) of the composition. The non-ionic surfactants comprise ethoxylated alkylphenols such as ethoxylated nonylphenols or octylphenoxypolyethoxyethanol. The cationic surfactants comprise ethylene oxide condensates of aliphatic amines or ethoxylated tallow amines. The surfactant may also comprise an ethoxylated amine. In the preferred embodiment of the invention, the surfactant is selected from the group consisting of Tomah E-18-5, Tomah E-18-15, Rhodameen VP 532/SPB, Trymeen 6607, and Triton X-100.

In another aspect of this embodiment of the invention, the cell membrane altering compound is present in the composition in an amount effective to substantially lyse or cause pore formation in cell membranes or walls. The cell membrane altering compound may inhibit phospholipid sensitive Ca+2 dependent protein kinase and attack cell membranes or alter membrane permeability or disrupt membranes. The cell membrane altering compound comprises polymyxin-beta-nonapeptide (PMBN), alkylglycoside or alkylthioglycoside, betaine detergent, quarternary ammonium salt, amine, lysine polymers, magainin, melittin, phospholipase $A_2$ or phospholipase $A_2$ activating peptide (PLAP). Alternatively, the cell membrane altering compound is an antibiotic such as polymyxin B sulfate or vancomycin or a mixture of polymyxin B1 and polymyxin B2. Preferably, the cell membrane altering compound comprises an alkylglycoside or an alkylthioglycoside such as octyl thioglucoside. The octyl thioglucoside may be present at a final concentration of at least 0.4%, and less than 1% (w/v)., preferably between 0.4% and 0.6% (w/v).

In another aspect of this embodiment of the invention, the composition further comprises a buffer salt. The buffer salt may be present in an amount sufficient to maintain a pH range from about 6.5 to about 9.0.

In another aspect of this embodiment of the invention, the composition further comprises other materials such as a defoaming agent, an agent to reduce non-specific binding of non-affinity labeled proteins, or a lysozyme.

In another aspect of this embodiment of the invention, the composition is in a form of an aqueous solution, preferably a concentrate. The composition preferably includes a buffer salt in an amount sufficient to maintain a pH range from about 6.5 to about 9.0.

In the preferred embodiment of the invention, the composition comprises Tomah E-18-15, Triton X100, and octyl beta thioglucopyranoside, most preferably 2% Tomah E-18-15, 2% Triton X100, and 6% octyl beta thioglucopyranoside in 500 mM HEPES (pH 7.5).

In another embodiment of the invention, a method is provided for recovering proteins or peptides from host cells comprising the steps of:

providing a source of cells having a desired protein or peptide;

providing a composition comprising at least one surfactant having a hydrophobic-lipophilic balance value in the range from about 11 to about 16 and at least one cell membrane altering compound; and contacting the cells with the composition in an amount effective to effect lysis of the cell and subsequent release of the protein or peptide.

In one embodiment of the invention, the cells comprise prokaryotic or eucaryotic cells such as bacterial, yeast, insect or plant cells. The cells may be in cultured medium and the composition is added to the medium without harvesting the cells from the medium. Alternatively, the cells may be harvested from the medium in the form of a pellet and the cell lysis composition is added to the pellet.

In another aspect of this embodiment of the invention, the method further comprising the step of separating the released protein or peptide, preferably by contacting the released protein or peptide with a substrate that binds the released protein or peptide. Preferably, the substrate comprises a magnetic or non-magnetic resin.

In another embodiment of the invention, a method is provided for recovering proteins or peptides from host cells comprising the steps of:

providing a source of cells having a desired protein or peptide;

providing a composition comprising at least one surfactant having a hydrophobic-lipophilic balance value in the range from about 11 to about 16 and at least one cell membrane altering compound;

providing a substrate for binding the protein or peptide;

contacting the cells with the composition in an amount effective to effect lysis of the cell and release of the protein or peptide;

contacting the released protein or peptide with the substrate under conditions effective for binding the release protein with the substrate;

washing the protein or peptide bound to the substrate; and recovering the protein or peptide bound to the substrate.

In another embodiment of the invention, an apparatus is provided for extracting and isolating a protein or peptide comprising:

a housing for holding one or more samples having a protein or peptide;

a composition comprising at least one surfactant having a hydrophobic-lipophilic balance value in the range from about 11 to about 16; and at least one cell membrane altering compound; and a substrate that binds the protein or peptide.

In one aspect of this embodiment of the invention, the housing comprises a container, a column, or a multi-well plate.

In another aspect of this embodiment of the invention, the substrate comprises a chromatographic resin or membrane.

The chromatographic resin is preferably magnetic.

In another aspect of this embodiment of the invention, a kit comprising the apparatus is provided for isolating proteins or peptides.

In another embodiment of the invention, a kit is provided comprising:
at least one surfactant having a hydrophobic-lipophilic balance value in the range from about 11 to about 16;
at least one cell membrane altering compound; and
directions for using the kit.

In one aspect of this embodiment of the invention, the surfactant and cell membrane altering compound are contained in a composition. Preferably, the composition may be an aqueous composition such a concentrate.

In another aspect of this embodiment of the invention, the kit may further include one or more of the following components: buffer, lysozyme, one or more washing buffers, one or more elution buffers, and substrate for binding proteins or peptides. The substrate may comprise a magnetic or non-magnetic chromatographic resin. The kit may further include means for detecting or quantifying the amount of protein or peptide present in the sample. The kit is useful for recovering proteins or peptides from host cells, for detecting for the presence or absence of a target protein or peptide, or for preparing cell extracts.

In another embodiment of the invention, a high throughput method is provided for recovering proteins or peptides from host cells comprising the steps of
providing one or more sources of cells having a desired protein or peptide;
providing a composition comprising at least one surfactant having a hydrophobic-lipophilic balance value in the range from about 11 to about 16 and at least one cell membrane altering compound; and
contacting each source of cells with the composition in an amount effective to effect lysis of the cells and subsequent release of the protein or peptide.

In one aspect of this embodiment of the invention, the method further comprising the step of separating the released protein or peptide from each source cell. The step may be performed by contacting the released protein or peptide with a substrate that binds to some or all of the release protein or peptide. The substrate may comprise a magnetic or non-magnetic resin.

In another aspect of this embodiment of the invention, the method further comprises measuring the activity or binding of the released protein or peptide.

In another embodiment of the invention, a high throughput method is provided for recovering proteins or peptides from host cells comprising the steps of:
providing one or more source of cells having a desired protein or peptide;
providing a composition comprising at least one surfactant having a hydrophobic-lipophilic balance value in the range from about 11 to about 16 and at least one cell membrane altering compound;
providing one or more substrates for binding the protein or peptide;
contacting each source of cells separately with the composition in an amount effective to effect lysis of the cell and subsequent release of the protein or peptide;
contacting the released protein or peptide from each source of cells with the substrate under conditions effective for binding some or all of the released protein with the substrate;
washing the protein bound to the substrate; and
recovering the protein bound to the substrate.

In one aspect of this embodiment of the invention, substrate comprises a magnetic or non-magnetic resin.

In another aspect of this embodiment of the invention, the method further comprises the step of measuring the activity or binding of the released protein or peptide.

In another embodiment of the invention, a high throughput method is provided for screening a library of proteins or peptides from sources of host cells, each source of host cell having a vector that encodes a protein or peptide member of the library, the method comprising the steps of:
providing a library of proteins or peptides from sources of host cells, each source of host cells having a vector that encodes a protein or peptide of the library;
providing a composition comprising at least one surfactant having a hydrophobic-lipophilic balance value in the range from about 11 to about 16 and at least one cell membrane altering compound;
providing one or more substrates for binding the protein or peptide;
contacting each source of cells with the composition in an amount effective to effect lysis of the cell and subsequently release of the protein or peptide;
contacting the released protein or peptide from each source of cells with the substrate under conditions effective for binding some or all of the released protein or peptide with the substrate;
washing the protein or peptide bound to the substrate; and
recovering the protein or peptide bound to the substrate.

In one aspect of this embodiment of the invention, the protein or peptides are mutants of a particular protein or peptide of interest.

In another aspect of this embodiment of the invention, the method further comprises the step of measuring the activity or binding properties of the protein or peptide.

In another aspect of this embodiment of the invention, the composition comprises Tomah E-18-15, Triton X100, and octyl beta thioglucopyranoside, preferably 2% Tomah E-18-15, 2% Triton X100, and 6% octyl beta thioglucopyranoside in 500 mM HEPES (pH 7.5).

In another embodiment of the invention, a method is provided for producing a cell extract from cultured cells without harvesting the cells from culture medium, the method comprising contacting the cell medium with an amount of composition effective to lyse the cells, the composition comprising
(a) at least one surfactant having a hydrophobic-lipophilic balance value in the range from about 11 to about 16; and
(b) at least one cell membrane altering compound.

These and other embodiments of the invention will become apparent in light of the detailed description below.

DESCRIPTION OF THE FIGURES

FIG. 1(a) is a bar graph that illustrates apparent cell culture densities of a bacterial solution treated with various formulations as described in Example 2.

FIG. 1(b) is a bar graph that illustrates the relative enzyme levels of enzyme in media and cell pellet upon treatment of an E. coli culture with various solutions as described in Example 2.

FIG. 2(a) is a bar graph that illustrates the release of enzyme into media using various detergents as described in Example 4.

FIG. 2(b) is a bar graph that illustrates the release of enzyme into media using various detergents in combination with polymyxin B as described in Example 4.

FIG. 3 is a bar graph that illustrates the release of enzyme by various Tergitol® detergent solutions in combination with polymyxin B as described in Example 5.

FIG. 9 is a photograph of a SDS-PAGE gel showing the relative degree of purity of proteins from high throughput purification of proteins using a 1× cell lysis reagent in different robotic platforms as described in Example 16.

FIG. 10 is a bar graph demonstrating JM109cell lysis in a high throughput assay described in Example 13.

FIG. 11 is a bar graph demonstrating CA7 cell lysis in a high throughput assay described in Example 13.

FIGS. 12A-B demonstrates the release of proteins in the presence (12B) and absence (12A) of lysozyme. Lane 1: High-RnaseHI; Lane 2: His-humanized Renilla luciferase; Lane 3: His-RNasin; Lane 4: His-thermostable firefly luciferase; Lane 5: His-methionyl tRNA synthetase; and Lane 6: His-beta-galactosidase.

DETAILED DESCRIPTION OF THE INVENTION

Figure 4:
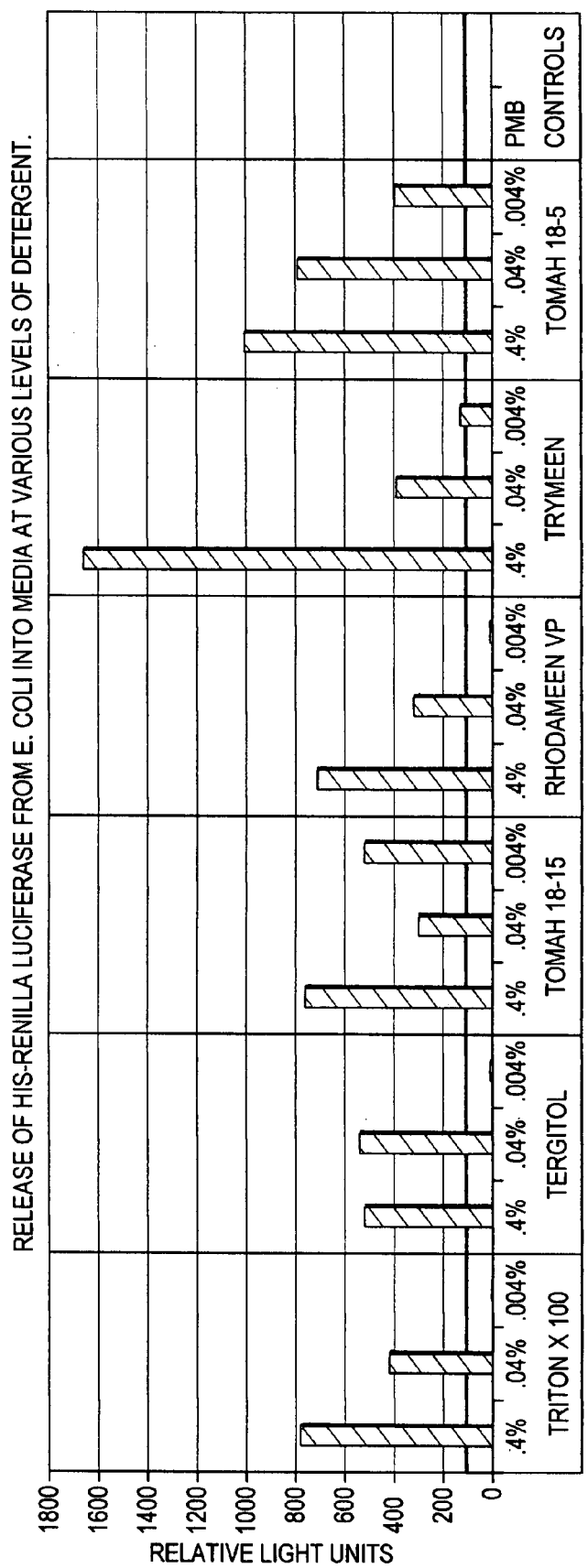
FIG. 4 is a bar graph that illustrates the release of protein from E. coli into media at different concentrations of detergents as described in Example 11.
Figure 5:
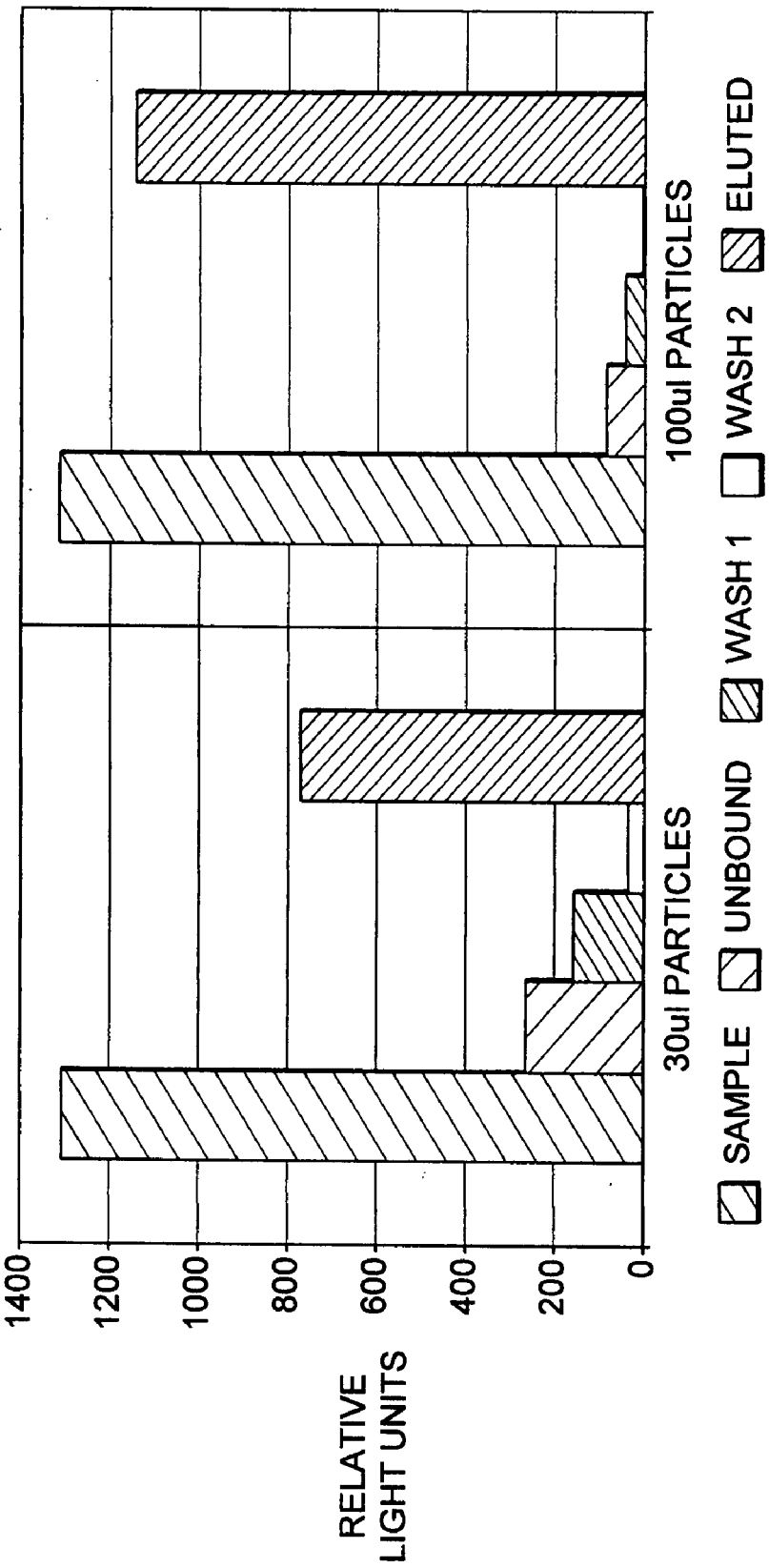
FIG. 5 is a bar graph that illustrates the relative capture and elution of protein released from E. coli in media using a cell lysis reagent containing Tomah® E18-15 detergent as described in Example 10.

The present invention provides compositions, methods, and kits that may be used in extracting and isolating protein and peptide molecules from a protein and/or peptide containing cell. It will be readily appreciated by those skilled in the art that, in accordance with the present invention, any cell, tissues, organs, populations of cells, etc. can be used as a protein and peptide source.

A. Definitions

In the description that follows, a number of terms used in the fields of molecular biology, biochemistry and protein chemistry are utilized extensively. In order to provide a clear and consistent understanding of the specification and claims, including the scope to be given such terms, the following definitions are provided.

As defined herein, the term "host cell" (used interchangeably with "host"), as used therein, refers to any prokaryotic or eukaryotic cell that produces the protein and/or peptide of interest. For examples of such hosts, see Maniatis et al., "Molecular Cloning: A Laboratory Manual," $2^{nd}$ Edition, Cold Spring Harbor Laboratory, Cold Spring Harbor, N.Y. (1982). Preferred prokaryotic hosts include, but are not limited to, bacteria of the genus Escherichia (e.g., E. coli), Bacillus, Staphylococcus, Agrobacter (e.g., A. tumefaciens), Streptomyces, Pseudomonas, Salmonella, Serratia, Caryophanon, etc. The most preferred prokaryotic host is E. coli. Bacterial hosts of particular interest in the present invention include E. coli strains K12, DH10B, DH5-alpha, HB101, JM109 and BL21(DE3)pLys. Preferred eukaryotic hosts include, but are not limited to, fungi, fish cells, yeast cells, plant cells and animal cells. Particularly preferred animal cells are insect cells such as Drosophila cells, Spodoptera Sf9, Sf21 cells and Trichoplusa High-Five cells; nematode cells such as C. elegans cells; and mammalian cells such as COS cells, CHO cells, VERO cells, 293 cells, PERC6 cells, BHK cells and human cells. In accordance with the invention, a host or host cell may serve as the cellular source for the desired protein and/or peptide molecule to be isolated.

The term "native conformation," as used herein, is defined as the tertiary or quaternary structure (or range of tertiary or quaternary structures) of the amino acid chain as it is known to exist in the biological host wherein the protein or peptide is naturally translated without intervention. It is generally assumed in the art that a protein or peptide in its native conformation will also possess all native functions and activities. Perturbation of the native conformation often, but not necessarily, leads to perturbation of the native function or activity, such proteins and peptides could also be referred to as denatured proteins and peptides. The structure of proteins or peptides will be considered to be perturbed for the purposes of this application if their native structure cannot be regained without significant manipulation (e.g. remolding techniques). Proteins and peptides that substantially maintain their native conformations have substantially all of their native functions and activities.

The term "soluble protein," as defined herein, is defined as a protein molecule which, in its current conformation, is adequately surrounded by solvent molecules so as not to form large aggregates with other protein molecules in a non-specific manner (e.g. precipitation, flocculation, etc). A contrasting term would be an insoluble protein to include transmembrane proteins, denatured proteins and proteins forming an inclusion body. Proteins or peptides that may be insoluble (form an inclusion body) in one solvent (e.g. an aqueous solvent), may be soluble in a different buffer system (e.g. 6M Urea).

The term "isolated" (as in "isolated protein molecule" or "isolated peptide molecule") means that the isolated material, component, or composition has been at least partially purified away from other materials, contaminants, and the like which are not part of the material, component, or composition that has been isolated. For example, an "isolated protein molecule" is a protein molecule that has been treated in such a way as to remove at least some of the contaminants (e.g., membrane fragments or nucleic acids) with which it may be associated in the cell, tissue, organ or organism. As one of ordinary skill will appreciate, however, a solution comprising an isolated protein and/or peptide molecule may comprise one or more buffer salts, solvents, e.g., water, and/or other protein and peptide molecules, yet the desired protein and peptide molecules may still be considered an "isolated" protein and peptide molecules with respect to its starting materials.

The term "cell lysis composition or reagent," as used herein, refers to a composition that effects lysis, rupture, or poration of the cells, tissues, or organisms used as the source of the protein and peptide molecules to be isolated, such that the soluble protein and peptide molecules (or portion thereof) that are contained in the cell, tissue, or organism source are released from the cell, tissue, or organism. According to the invention, the cells, tissues, or organisms need not be completely lysed/disrupted/permeabilized, and all of the protein and peptide molecules contained in the source cells, tissues or organisms need not be released therefrom. Preferably, a cell disrupting or cell lysis composition will release at least 50% or more of the total protein or peptide molecules of interest (soluble and insoluble) that are contained in the cell, tissue, or organism.

The term "cell membrane altering compound," as used herein, refers to any compound or combination of compounds that alters cell membrane permeability or disrupts the integrity of (i.e., lyses or causes the formation of pores in) the membrane and/or cell wall of the cellular source of protein and peptide molecules by any mechanism so as to release some or all of the desired protein from the cellular source. Generally, cell membrane altering compounds include a variety of agents such as antibiotics like polymyxin B (e.g., polymyxin B1 and polymyxin B2), and polymyxin-beta-nonapeptide (PMBN); alkylglucoside or alkylthioglucoside, such as Octyl-β-D-1-thioglucopyranoside (see U.S. Pat. No. 6,174,704 herein incorporated by reference in its entirety); betaine detergents such as carboxypropylbetaine (CB-18); quarternary ammonium salts such as trimethyloctadecyl ammonium bromide (TMA-18); protamines; amines such as triethylamine (TEA) and triethanolamine (TeolA); and lysine polymers such as polylysine pore-forming (antibacterial) peptides, e.g., lantibiotic nisin; and neurotoxins such as magainin, melittin, phospholipase $A_2$ and phospholipase $A_2$ activating peptide (PLAP), which result in poration and/or enlarging existing pores of cell membranes. See Morbe et al. Microbiol. Res. (1997) vol. 152, pp. 385-394, which is incorporated herein by reference in its entirety.

The term "hydrophobic-lipophilic balance value," or (HLB) as used herein, refers to a classification of surfactants that is related to their behavior and solubility in water. HLB value may be calculated for a non-ionic surfactant or may be determined experimentally for other surfactants. The HLB value is on a scale of one to 40. As the HLB increases, there are more hydrophilic groups in the surfactant and the surfactant is more water-soluble. Generally, an HLB of 3-6 indicates a water-in-oil emulsifier, an HLB of 7-9 indicates a wetting agent, an HLB of 8-18 indicates an oil-in-water emulsifier, an HLB of 13-15 indicates a detergent, and an HLB of 15-22 indicates a solubilizer. The following references provide more information about HLB: Griffin, W C, "Calculation of HLB Values of Non-Ionic Surfactants," *Journal of the Society of Cosmetic Chemists,* 5 (1954), 249-256; Griffin, W C, "Classification of Surface-Active Agents by 'HLB'," *Journal of the Society of Cosmetic Chemists,* 1 (1949), 311-326; *The Atlas HLB System,* 4th printing, Wilmington, Del., Atlas Chemical Industries, 1963; "Emulsions", *Ullmans's Encyclopedia of Industrial Chemistry,* 5th ed 1987; Fox, C., "Rationale for the Selection of Emulsifying Agents", *Cosmetics & Toiletries* 101.11 (1986), 25-44; Garcia, A., J. Lachaise, and G. Marion, "A Study of the Required Hydrophile-Lipophile Balance for Emulsification", *Langmuir* 5 (1989):1215-1318; and Griffin, W. C. "Emulsions", *Kirk Othmer Encyclopedia of Chemical Technology,* 3rd ed 1979.

Other terms used in the fields of protein chemistry, biochemistry, recombinant DNA technology, molecular biology and cell biology as used herein will be generally understood by one of ordinary skill in the applicable arts.

B. Sources of Proteins and Peptides

The methods, compositions and kits of the invention are suitable for isolation of protein and peptide molecules from any cellular source, including a variety of cells, tissues, organs or organisms, which may be natural or which may be obtained through any number of commercial sources (including American Type Culture Collection (ATCC), Manassas, Va.; Jackson Laboratories, Bar Harbor, Me.; Cell Systems, Inc., Kirkland, Wash.; Advanced Tissue Sciences, La Jolla, Calif.). Cells that may be used as cellular protein and peptide sources may be prokaryotic (bacterial, including members of the genera *Escherichia* particularly *E. coli*), *Serratia, Salmonella, Staphylococcus, Streptococcus, Clostridium, Chlamydia, Neisseria, Treponema, Mycoplasma, Borrelia, Bordetella, Legionella, Pseudomonas, Mycobacterium, Helicobacter, Agrobacterium, Collectotrichum, Rhizobium,* and *Streptomyces*) or eukaryotic (including fungi or yeasts, plants, protozoans and other parasites, and animals including humans and other mammals). Also suitable for use as sources of protein and peptide molecules are mammalian tissues or cells such as those derived from brain, kidney, liver, pancreas, blood, bone marrow, muscle, nervous, skin, genitourinary, circulatory, lymphoid, gastrointestinal and connective tissue sources (e.g. of endodermal or ectodermal origin), as well as those derived from a mammalian (including human) embryo or fetus. Appropriate sources of protein and peptide may also be any of the above cells harboring plasmids, phagemids, cosmids, viruses, phages, or other DNA molecules capable of expressing the desired proteins and peptides. These cells, tissues and organs may be normal, primary, transformed, or established cell lines, or they may be pathological such as those involved in infectious diseases (caused by bacteria, fungi or yeast, viruses including AIDS) or parasites, in genetic or biochemical pathologies (e.g., cystic fibrosis, hemophilia, Alzheimer's disease, schizophrenia, muscular dystrophy or multiple sclerosis), or in cancers and cancerous processes. The methods, compositions and kits of the invention are well-suited for isolation of small soluble proteins and peptides, e.g. those of 1000 kD or less, preferably, about 1-100 kD, most preferably, about 1-50 kD. For larger molecular weight proteins, e.g, those greater than 1000 kD, lysozyme may be used as an adjunct to assist in the release of these proteins. The methods of the invention are particularly well suited for isolation of protein or peptide molecules expressed in a biological host, which form an inclusion body. To release protein or peptide molecules from inclusion bodies, reagents such as urea or guanidine-HCl may be used as an adjuvant to assist in the release of proteins and peptide molecules associated with the inclusion bodies.

In a particularly preferred aspect, the methods of the invention are useful in the isolation of recombinant protein and peptide molecules expressed from DNA incorporated in a host capable of expressing said proteins and peptides. Particularly preferred protein and peptide molecules are part of a protein or peptide library. Such libraries include, but are not limited to populations of completely novel amino acid sequences encoded by random polynucleotide sequences or can be libraries or groups of randomly generated mutant proteins and peptides. Other cells, tissues, viruses, organs and organisms that will be familiar to one of ordinary skill in the art may also be used as sources of protein and peptide molecules for the extraction and preparation of isolated protein and peptide molecules according to the present invention.

b. Cell Lysis Composition

The present invention relates to a cell lysis composition that disrupts or lyses one or more cells. The cells may be present in cell media or as a frozen or unfrozen pellet. In one embodiment of the invention, the cell lysis composition comprises: (a) at least one surfactant having a hydrophobic-lipophilic balance value in the range from about 11 to about 16; and (b) at least one cell membrane altering compound. The composition may be in a form of an aqueous solution or solid that is reconstituted in water or buffer solution prior to use. The preferred form of the cell lysis composition is an aqueous solution such as a 1× solution or a concentrate solution, e.g., 10× (particularly preferred). The 1× solution may be added directly to cell pellets while the concentrate may be added directly to the cell media. When a 10× concentrate solution is used, 1 volume of the 10× solution would preferably be mixed with 9 volumes of the cell media to provide a final 1× concentration of the cell lysis reagent in the cellular mixture.

The surfactant is present in the cell lysis composition in an amount ranging from about 0.001 to about 10% (w/v) of the composition, preferably ranging from about 0.01 to about 10%(w/v), and most preferably about 1 to about 10% (w/w). When a 10.times. concentrate form of the cell lysis reagent is added to cell media in certain applications described herein, the preferred final concentration of the surfactant ranges from about 0.1 to about 1%(w/v). The surfactant may be selected from the group consisting of non-ionic surfactants, cationic surfactants, and mixtures thereof having a hydrophobic-lipophilic balance value ranging from about 11 to about 16. Commercial sources of such surfactants can be found in McCutcheon's EMULSIFIERS AND DETERGENTS, North American Edition, 2002, McCutcheon Division, MC Publishing Company, also incorporated herein by reference. Suitable, but non-limiting, examples of non-ionic surfactants include alkyl alcohol ethyoxylates, alkyl ester ethyoxylates, polypropylene oxide, sorbitol alkyl esters, glycerol alkyl esters, ethylene oxide/ propylene oxide block co-polymers; poly(oxyethylene) alkyl ethers such as those sold under the tradename BRIJ available from ICI Americas (Wilmington, Del.), poly(oxyethylene) sorbitan esters sold under the tradename TWEEN (ICI Americas, Wilmington, Del.). The preferred non-ionic surfactants include ethoxylated alkylphenols such as ethoxylated nonylphenols sold under the tradename TERGITOL NP (Union Carbide, Danbury, Conn. or octylphenoxypolyethoxyethanol sold under the tradename TRITON X (Rohm & Haas, Philadelphia, Pa.).

Suitable, but non-limiting, examples of cationic surfactants comprise ethylene oxide condensates of aliphatic amines or ethoxylated tallow amines. The preferred cationic surfactants include the ethoxylated amines sold under the tradename TRYMEEN from Henkel Corp. (Cincinnati, Ohio), and the Tomah E series available from TOMAH Products, Inc. (Milton, Wis.).

Some surfactants suitable, but non-limiting, for use in our present invention, are characterized as having both non-ionic and cationic properties such as ethoxylated fatty amines sold under the tradename RHODAMEEN VP, available from Rhodia (Cranberry, N.J.)

Suitable, but non-limiting, examples of cell membrane altering compounds include antibiotics, alkylglycoside or alkylthioglycoside, betaine detergents, quaternary ammonium salts, amines, short-chained phospholipids such as 1,2-diheptanoyl-sn-glycero-3-phosphocholine (DHPC) and pore-forming peptides. Representative antibiotics include, without limitation, polymyxin B sulfate or vancomycin. A preferred antibiotic is a mixture of polymyxin B1 and polymyxin B2, commonly referred to as polymyxin B. Any suitable amount of cell membrane altering compound may be used in the cell lysis composition that is sufficient to lyse or cause pore formation in the host cell membrane or cell wall to release some or all of the desired protein or peptide. When Polymyxin B, the preferred cell membrane altering compound is used in the cell lysis composition, it is generally present in an amount ranging from about 0.025 to about 0.25% (w/v).

Another preferred cell membrane altering compound is an alkylglycoside or alkylthioglycoside. Representative alkylglycoside or alkylthioglycoside includes, without limitation, octyl-β-D-1-thioglucopyranoside (or octyl thioglucoside). U.S. Pat. No. 6,174,704 (incorporated herein by reference in its entirety) provides a method for the preparation and extraction of a recombinant protein from a host cell. The method uses a reagent solution consisting essentially of 1% octyl thioglucoside (OTG) to lyse the cell and concurrently extract the protein of interest from other host cellular proteins. In the present invention, it has been unexpectedly discovered that in addition to OTG, at least one surfactant is required to achieve both efficient cell lysis and satisfactory protein purity. Furthermore, it has been unexpectedly discovered that although there is greater lysis with higher concentration of OTG, such as 1% (w/v) used in U.S. Pat. No. 6,174,704, cell lysis composition with such high concentration of OTG also has a greater tendency to inactivate certain proteins. Therefore, a careful balance between efficient cell lysis and protein activity is very important. In one embodiment of the invention, OTG is used as a cell membrane altering compound in the 10× cell lysis composition added directly to cell media, wherein the desirable concentration of OTG is at least 4%, and less than 10% (w/v), preferably between 4 and 6% (w/v). Accordingly, the optimal final working concentration of OTG in the 1× cell lysis composition is at least 0.4%, and less than 1% (w/v), preferably between 0.4% and 0.6% (w/v). However, if the native structure or activity of the protein or peptide is not required, no limitation on the lysis/disruption reagent is required. The cell lysis composition preferably includes buffer salts in an amount effective to maintain a pH from about 6.5 to about 9.0 in the cell media or suspension (when cell pellets are suspended in the cell lysis composition), preferably a pH ranging from about 7.0 to about 8.0. Suitable, but non-limiting, buffers include HEPES, PIPES, Tris-Hydrochloride (Tris-HCl), and MOPS.

Optional components may be included as part of the composition or as an adjuvant to be added separately, depending on what subsequent purification procedures would be performed. Optional components include a defoaming agent at a concentration of about 1%; enzymes such as lysozyme, lyticase, zymolyase, neuraminidase, streptolysin, cellulysin, mutanolysin, chitinase, glucalase or lysostaphin may be used, at a concentration of about 0.1 to 5 mg/ml; one or more inorganic salts such as sodium chloride, potassium chloride, magnesium chloride, calcium chloride, lithium chloride, or praseodymium chloride at a concentration of about 1 mM to 5M; protease inhibitors (e.g., phenylmethylsulfonyl fluoride, trypsin inhibitor, aprotinin, pepstatin A), reducing reagents (e.g., 2-mercaptoethanol and dithiothreitil) at concentrations of 0.1 to 10 mM; chelating agents (e.g., disodium ethylenediaminetetraacetic acid ($Na_2EDTA$), EGTA, CDTA, most preferably at a concentration of about 1 mM or less); one or more ribonucleases (RNase A, T1, T2, and the like) at concentrations ranging from 1 to 400 ug/ml, or any combination of the foregoing. DNase I concentrations may range from 1 to 100 units (10,000 units/mg).

c. Methods

The present invention also relates to methods for isolating proteins from host cells. Methods according to this aspect of the invention comprise contacting the cells with a cell lysate composition as described herein, which results in cell lysis and subsequent release of all or a portion of the desired protein. The released protein may be further separated from the lysate. In one embodiment of the invention, a method is provided for recovering proteins from host cells comprising the steps of:

providing a source of cells having a desired protein;

providing a composition comprising at least one surfactant having a hydrophobic-lipophilic balance value in the range from about 11 to about 16 and at least one cell membrane altering compound; and contacting the cells with the composition in sufficient amount to effect lysis of the cell and subsequent release of the protein.

In practicing this invention, any suitable amount of the composition may be used that is effective to lyse the cell by disrupting the cellular membrane/cell wall integrity and result in the subsequent release of the desired protein in whole or in part from the cellular source. In practicing the invention, the composition provides for the disruption of the cell membrane or cell wall integrity without substantially perturbing the native conformation or function of the desired proteins and peptides, so that a protein or peptide having the native conformation, or substantially the native conformation may be collected. However, if the native structure of the protein or peptide is not required, then no limitation on the lysis/disruption reagent is required. Generally, the concentration of the surfactant in the cellular mixture ranges from about 0.001 to about 10% %(w/v), usually from about 0.01 to about 10% (w/v), and preferably from about 0.1 to about 1% (w/v). In another embodiment of the invention, a method for recovering proteins from host cells are provided and which further include a step for separating the desired released protein from the lysate. The method comprises the steps of:

providing a source of cells having a desired protein;

providing a composition comprising at least one surfactant having a hydrophobic-lipophilic balance value in the range from about 11 to about 16 and at least one cell membrane altering compound;

providing a substrate for binding the protein;

contacting the cells with the composition in an amount effective to lyse the cell and release the protein;

contacting the released protein with the substrate under conditions effective for binding the released protein with the substrate;

washing the protein bound to the substrate; and recovering the protein bound to the substrate.

The separation of the released protein may be accomplished by any suitable method known in the art, including protein purification or chromatographic techniques using substrates, e.g., magnetic or non-magnetic resins, that bind to the protein. In practicing this invention, the desired protein may be separated and further purified using affinity chromatography (e.g., nickel or GST resins), ion-exchange chromatography, hydrophobic interaction chromatography, precipitation (e.g., with PEI, PEG or ammonium sulfate) and the like. Suitable chromatographic resins are described for instance in U.S. patent application No. 60/419,614, filed Oct. 18, 2002, entitled "Compositions and Methods of Separating Molecules" that is incorporated by reference in its entirety. The isolated protein may be sufficiently pure for intended purposes or may be subjected to further purification procedures (e.g. resins, antibodies, etc). Such additional purification may facilitate removal of unwanted contaminants such as nucleic acids, other proteins and peptides, lipids, nucleotides, oligonucleotides, or compounds or compositions which may inhibit the activity of or further manipulation of the protein and peptide molecule (e.g., labeling, cleaving via proteolysis, detection and quantitation of enzyme activity, etc). In any event, such further purification need not take place and thus the protein obtained by the method of the invention may be manipulated directly by standard biochemistry and protein chemistry techniques.

In a preferred aspect of the invention, one or more additional purification compositions (e.g., ion exchange resins, affinity resins, magnetic beads or resins, antibodies, nickel resins, GST resins, etc) are utilized in combination with the separation matrix in accordance with the invention. Such additional purification may be accomplished in separate procedures, although in a preferred aspect, the additional purification is accomplished simultaneously or in conjunction with the separation method of the invention. In one aspect, the one or more separation matrices and the one or more protein and peptide purification compositions are associated in series, in a fluid channel, such that a sample containing the desired protein and peptide molecules may pass from one matrix to another.

The released protein may be separated and/or purified in any suitable format such as a column format including mini-columns, a tube format, a well format, a multi-well plate format, etc. In one aspect of this invention, cell lysis and separation would occur within the same container. One particularly preferred embodiment would include the extraction and purification of a protein or peptide from host cells in a high throughput purification format as described herein. For instance, the substrate may be added to the cell lysate contained in a well. The substrate is then incubated with the cell lysate for a certain time period to allow the released protein to bind to the substrate. Thereafter, the lysate may be removed and the substrate bound protein may be washed one or more times with a wash buffer or solution. The protein bound to the substrate may then be recovered by washing the substrate one or more times with an elution buffer or solution. In another aspect of this invention, the cell lysate may be filtered through the substrate contained in a mini-column. After a predetermined time period to allow the protein to bind to the substrate, the substrate may be washed one or more times with any suitable wash buffer or solution and the bound protein may be eluted from the substrate by washing the substrate one or more times with any suitable elution buffer or solution. Unwanted materials such as lipids, nucleic acids, lysis composition components or any other substance which may inhibit further manipulation or analysis of protein and peptide molecules may be removed with any suitable wash buffer or solution which allows the desired protein and peptide molecules to be retained on the immobilized purification composition. Any suitable elution buffer or solution for removing the desired protein and peptide molecules from the immobilized purification composition may be used to isolate the purified protein and peptide molecules. Any of these procedures may be translated into a high throughput purification format for purification of single or multiple types of proteins or peptides using for instance a 96 well plate. Host cells can be added individually into the wells and lysed with the cell lysis reagent of the invention. The lysed mixture from each well can then be pipetted into separate wells having substrates, e.g., chromatographic resins that bind to the protein or peptides. After washing the substrate one or more times with a washing buffer to remove any unwanted materials, the proteins may then be eluted from the substrate by washing the substrate one or more times with an elution buffer.

In another embodiment of the invention, a method is provided for screening libraries of protein molecules in a high throughput format. For example, a library of random or mutated polynucleotide sequences may be screened for enzymatic activity or binding properties in a 96 well plate, using the described invention. Colonies of bacteria, each containing a plasmid encoding one member of the library, may be lysed with the lysis composition after induction of protein synthesis and the resulting released proteins are separated using a substrate that binds to the protein. After washing the substrate to remove any unwanted materials, the protein molecules may then be eluted from the substrate using a buffered aqueous solution and/or centrifugation and collected in the wells of a 96 well plate. Reagents containing desired ligands or substrates may be added to each well of the 96 well plate, and presence of activity or binding may then be measured by any methods deemed appropriate for the activity or binding properties desired.

In another embodiment the invention, a method is provided for screening libraries of randomly or systematically generated mutants of a particular protein or peptide of interest. A library of mutants could be screened efficiently for relative enzymatic activity using the 96-well lysis plate. Additionally, screening can be accomplished by immobilizing the proteins or peptides of the invention onto a scaffold such as multi-well plate, chip, slide, wafer, filter, sheet, tube, and the like. These scaffolds containing the immobilized protein or peptides of the invention, can be contacted with a composition that either binds to protein or peptide molecules (e.g. antibodies), is bound by the protein or peptide molecules (e.g., ligands) or causes a change in a measurable parameter (e.g. luminescence, color change, fluorescence, chemiluminescence, etc.).

d. Apparatus and Kits

The invention also relates to an apparatus for use in extracting and isolating protein. Thus in one embodiment of the invention, the apparatus comprises:

(a) a housing capable of receiving a sample to be tested:

(b) a composition comprising at least one surfactant having a hydrophobic-lipophilic balance value in the range from about 11 to about 16; and at least one cell membrane altering compound; and (c) at least one substrate that binds proteins.

Suitable, but non-limiting, examples of housing include containers such as boxes, cartons, tubes, microspin tubes, microfuge tubes, spin cartridges, multi-well plates, vials, ampules, bags, and the like.

Representative examples of substrates that bind proteins include, without limitation, chromatographic resins or non-resins that bind proteins or peptides. Examples of chromatographic resins that bind proteins or peptides include ion exchange resins, affinity resins, magnetic beads or resins, antibodies, nickel resins, GST resins, and the like. These resins may further have bound thereto antibodies, protein ligands, compositions capable of covalently attaching themselves to the protein or peptides, and the like. Suitable chromatographic resins are described for instance in U.S. Patent application No. 60/419,614, filed Oct. 18, 2002, entitled "Compositions and Methods of Separating Molecules" that is incorporated by reference in its entirety. In another embodiment of this invention, the apparatus further comprises means for detecting or quantitating the amount of protein in a sample such as antibodies which bind to the protein or peptides; substrates for said protein or peptides; ligands for said proteins or peptides; cofactors for said protein; enzymes which modify said proteins or peptides, and compositions which modify said proteins or peptides.

The invention also relates to kits for use in isolating protein and peptide molecules. Such kits of the invention may comprise one or more components, which may be contained in or include one or more containers such as boxes, cartons, tubes, microspin tubes, microfuge tubes, spin cartridges, multi-well plates, vials, ampules, bags, and the like. In one embodiment, the inventive kits may comprise:

(a) a composition comprising at least one surfactant having a hydrophobic-lipophilic balance value in the range from about 11 to about 16; and at least one cell membrane altering compound; and (b) directions for using the kit.

The composition used in the kit may be in the form of a solid or an aqueous solution in concentrated or ready-to-use diluted form.

In another embodiment of the invention, a diagnostic kit for detecting for the presence of a protein in a sample is provided. The kit comprises:

(a) a composition comprising at least one surfactant having a hydrophobic-lipophilic balance value in the range from about 11 to about 16; and at least one cell membrane altering compound;

(b) means for detecting or quantifying the amount of protein present in the sample; and (c) directions for using the kit.

The kits may further comprise additional protein and/or peptide purification compositions, wash buffers, elution buffers; one or more additional components or reagents that may be useful in further protein processing, analysis, or use of the protein and peptide molecules isolated or purified according to the invention, for example components or reagents useful in protein and peptide purification, labeling, or detection. Such reagents or components may, for example, include one or more substrates that bind amino acid sequences to aid in purification (e.g., nickel resins, and GST binding resins), or other reagents that will be familiar to one of ordinary skill in the art. The detection and/or quantification of the protein as well as ascertaining its purity level can be performed by any conventional means known in the art. For instance, detecting and/or quanitifying proteins or peptides can be performed by measuring activity or binding of the protein or peptide by any method including immunoassays or by SDS-PAGE analysis. See for instance, R. K. Scopes in "Protein Purification: Principles and Practice," $3^{rd}$ Ed., Springer-Verlag, 1994.

EXAMPLES

Example 1

Preparation of Cell Lysis Reagent

In this Example, several representative cell lysis reagents are described. For cell pellets, a cell lysis reagent at 1× concentration aqueous formulation is preferably used. For cell media, a cell lysis reagent at 10× concentration is preferable.

(a) Cell Lysis Reagent at 1× Concentration:

This 1× aqueous formulation is useful for extracting proteins or peptides from cell pellets (frozen or non-frozen). The amount of the formulation added to the pellets is generally based on the optical density of the cells. For example, 200 ul of 1× formulation is used for the lysis of cells with an OD600 of 1.8/1 ml. The formulation contains the following components:
100 mM HEPES, pH 7.5,
1% Triton X-100 (Sigma, St. Louis, Mo., Cat# T-9284)
1% Mazu DF204 (defoaming agent, PPG Industries, Gurnee, Ill., Cat# 213306-2)
0.4% Tomah (purified Tomah E-18-15, Bioaffinity systems, Roscoe, Ill., Cat# 016483)
10 mM imidazole (Sigma, St. Louis, Mo.; Cat# 1-2399)
380U Polymyxin B sulfate (Sigma, St. Louis, Mo.; Cat # P-1004, lot 22K2517)

(b) 1× Cell Lysis Reagent Containing Lysozyme

This 1× aqueous formulation containing is useful for improving the extraction of larger proteins or peptides (>400 kD) from cell pellets (frozen or non-frozen). The amount of the formulation added to the pellets is generally based on the optical density of the cells. For example, 200 ul of 1× formulation is used for the lysis of cells with an OD600 of 1.8/1 ml. The formulation contains the following components:
100 mM HEPES, pH 7.5,
1% Triton X-100 (Sigma, St. Louis, Mo., Cat# T-9284)
1% Mazu DF204 (defoaming agent, PPG Industries, Gurnee, Ill., Cat# 213306-2)
0.4% Tomah (purified Tomah E-18-15, Bioaffinity systems, Roscoe, Ill., Cat# 016483)
10 mM imidazole (Sigma, St. Louis, Mo.; Cat# 1-2399)
380U Polymyxin B sulfate (Sigma, St. Louis, Mo.; Cat # P-1004, lot 22K2517)
Optionally, Lysozyme can be added (Sigma, St. Louis, Mo.)

Example 2

Release of Renilla Luciferase from E. coli

Cytoplasmic protein, as measured by the enzyme Renilla Luciferase, is released from E. coli cells when the cells are treated with a solution containing detergent and Polymyxin B. Surprisingly, this release of enzyme is not accompanied by general cell lysis as measured by observation of the optical density of the culture during the treatment.

E. coli bacteria expressing His-tagged Renilla Luciferase were grown in Luria Broth [L Broth]+10 ng/ml tetracycline [Tet] [50 ml of media in a 250 ml flask] at 37° C. overnight in a shaking incubator rotating at 200 RPM. The E. coli strain was prepared by transforming E. coli with a vector expressing histidine-tagged Renilla luciferase. The vector was constructed by conventional methods. See Maniatis et al., "Molecular Cloning: A Laboratory Manual," $2^{nd}$ Edition, Cold Spring Harbor Laboratory, Cold Spring Harbor, N.Y. (1982). Following overnight culture the bacterial cells were diluted 1:100 into fresh L broth+Tet and grown to a density of 0.6 at 600 nm [OD 600 0.6] at 37C on the shaking incubator. Renilla expression was induced by addition of isopropyl-beta-D-thiogalactopyranoside (IPTG) from a 1M filter sterilized solution to a final concentration of 1 mM. The culture was grown for 4 additional hours at 37C on the shaking incubator before use.

A 10 mg/ml solution of lysozyme [Sigma L 6876, lot 51K7028] was prepared by dissolving solid enzyme in a 20 mM Tris-HCl buffer, pH 7.3.

A 10× cell lysis reagent [CLR formulation A] formulation was generated by mixing: 25 ml of 1 M HEPES buffer pH 7.5, 5 ml of Triton X 100 [Sigma T9284 St. Louis Mo., lot 118H0297), 2 ml of Tomah E-18-15 [as supplied by Tomah Chemical Company, Tomah Wis.], 25 mg of Polymyxin B [Sigma P-1004, lot 22K2517] and adjusting the solution to 50 ml with the addition of nanopure filtered water.

One ml of the Renilla luciferase expressing E. coli culture was added to each of 12 tubes, labeled 1 through 12: tubes 1-3, no further addition; tubes 4-6, 10 ul of 10 mg/ml lysozyme; tubes 7-12, 100 ul of CLR formulation A, and; tubes 10-12, 100 ul of CLR formulation A and 10 ul of 10 mg/ml lysozyme. These tubes were inverted 10 times and then visually inspected for the level of turbidity: Tubes 1-3, solution very turbid; tubes 4-6, solution very turbid; tubes 7-9, solutions slightly less turbid, and; tubes 10-12, solution much less turbid.

900 ul of 20 mM Tris-HCl pH 7.3 and 100 ul of the corresponding solutions were added to each of 12 disposable plastic cuvettes. After the instrument background was set to zero with a 20 mM Tris-HCl pH 7.3 solution at an optical density of 600 nm (OD600), and the optical density of the solutions was measured. The following readings were recorded:

| Tube # | OD600 |
|---|---|
| Tube 1 | 0.3193 |
| Tube 2 | 0.3266 |
| Tube 3 | 0.3266 |
| Tube 4 | 0.3264 |
| Tube 5 | 0.3261 |
| Tube 6 | 0.3033 |
| Tube 7 | 0.1779 |
| Tube 8 | 0.1789 |
| Tube 9 | 0.1779 |
| Tube 10 | 0.0020 |
| Tube 11 | 0.0012 |
| Tube 12 | 0.0013 |

These data are presented graphically in FIG. 1A following adjustment of the measured absorbance for the dilution that was performed on the culture.

The dramatic reduction in optical density of the solutions in tubes 10-12 is very indicative of complete cell lysis. While there was a measurable reduction in the optical density of the solution in tubes 7-9, the reduction in optical density was not as dramatic as that seen in tubes 10-12. These data are presented graphically in FIG. 1A.

The remaining solutions in tubes 1-12 were spun at full speed in a microcentrifuge at 4C for 10 min and the supernatants transferred to fresh, labeled tubes (NOTE: very little pellet was seen in tubes 10-12, a small amount [approx 20 ul] of the supernatant was allowed to remain in these tubes to prevent accidental disturbance of the pellet). The pellets were resuspended in 800 ul of a solution consisting of: 1 ml of CLR formulation A, 9 ml of nanopure water, and 100 ul of 10 mg/ml lysozyme.

Three ml of Renilla Luciferase Assay Buffer [Promega Corp, Madison Wis. E290A, lot 13327801] was mixed with 30 ul of Renilla Luciferase Assay Substrate [Promega Corp. E289A, 13358301] to create Renilla Luciferase Assay Reagent, and 100 ul sample of the reagent placed in each of 24 luminometer tubes. Two microliter samples of the reserved supernatants and 2 microliters from the resuspended pellets was then added to their respective tubes. The tubes were mixed by vortex for 3 sec and light production was measured using a Turner TD 20/20 Luminometer (Turner Designs, Sunnyvale, Calif.). The following relative light unit (RLU) measurements were observed:

| Sample Tube Measured | Relative light Units, Supernatant Sample | Relative Light Units Resuspended Pellet Sample |
| --- | --- | --- |
| 1 | 0.033 | 53.15 |
| 2 | 0.033 | 64.56 |
| 3 | 0.020 | 59.32 |
| 4 | 0.053 | 58.41 |
| 5 | 0.074 | 60.99 |
| 6 | 0.048 | 72.03 |
| 7 | 87.43 | 1.152 |
| 8 | 69.71 | 1.208 |
| 9 | 67.06 | 1.215 |
| 10 | 68.03 | 1.002 |
| 11 | 75.64 | 1.116 |
| 12 | 97.51 | 1.101 |

As expected, essentially all of the Renilla Luciferase activity was found in the pellet samples in tubes 1-3. Also as expected, essentially all of the Renilla Luciferase activity was found in the pellet sample in tubes 4-6, as there was very little optical density reduction observed in these solutions and lysozyme by itself is not expected to lyse *E. coli* cells. Also as expected, essentially all of the Renilla Luciferase activity was found in the supernatant samples in tubes 10-12 as the drastic reduction in optical density indicated that these cells were fully lysed and the Renilla Luciferase, a protein in the cytoplasm of these cells, would then be released into the media. Surprisingly, while the solutions in tubes 7-9 showed only a modest reduction in optical density (suggesting that the cells were essentially intact) almost all of the Renilla Luciferase activity was found in the supernatant samples indicating that the treatment given to these cells released the enzyme to the media. This data is shown graphically in FIG. 1B.

Example 3

Screening of Detergents for the Ability to Release Enzymes into Media from *E. coli* Without Inactivation of the Enzyme In this example, a number of detergents were tested for their ability to release cytoplasmic protein from *E. coli* cells alone and in combination with Polymyxin B.

The following stock detergent solutions were prepared:

Two grams of deoxycholic acid, sodium salt [Sigma D 6750, 102H0811] was dissolved in deionized water to produce a 4% (v/v) DOC solution.

Two grams of Lauryl Sulfate, sodium salt [Sigma L 4390, 73H0057] was dissolved in deionized water to produce a 4% (v/v) SDS solution.

Two grams of Tomah E-14-5 [Tomah Chemical Company, lot 71002-1] was dissolved in deionized water to produce a 4% (v/v) Tomah E-14-5 solution.

Two grams of Tomah E-14-2 [Tomah Chemical Company, lot 70224-1] was dissolved in deionized water to produce a 4% (v/v) Tomah E-14-2 solution.

Two grams of Tomah E-18-15 [Tomah Chemical Company, lot 60911-1] was dissolved in deionized water to produce a 4% (v/v) Tomah E-18-15 solution.

Two grams of Tomah E-18-5 [Tomah Chemical Company, lot 60911-1] was dissolved in deionized water to produce a 4% (v/v) Tomah E-18-5 solution Two milliliters of Rhodameen PN-430 [Rhodia, North American Chemicals lot SP8B017049] was mixed with deionized water to produce a 4% (v/v) Rhodameen PN solution.

Two milliliters of Rhodameen VP532/SPB [Rhodia, North American Chemicals lot SP8B017049] was mixed with deionized water to produce a 4% (v/v) Rhodameen VP solution.

Two milliliters of Trymeen 6607 [Kraft Chemical Company, lot 8A0120] was mixed with deionized water to produce a 4% (v/v) Trymeen 6607 solution.

Two milliliters of Triton W-30 [Sigma Chemical Co, W-30, lot 18F0766] was mixed with deionized water to produce a 4% (v/v) Triton W-30 solution.

Ten milliliters of Tween 20 [Sigma Chemical Company P7949, lot 15H09293] was mixed with deionized water to produce a 20% (v/v) Tween 20 solution.

Ten milliliters of Triton X-100 [Sigma Chemical Company, T9284, lot 118H0297] was mixed with deionized water to produce a 20% (v/v) Triton X-100 solution.

Ten milliliters of Tergitol NP-9 [Sigma Chemical Company, NP-9, lot 41KO156] was mixed with deionized water to produce a 20% (v/v) Tergitol NP-9 solution.

Ten milliliters of Tween 80 [Sigma Chemical Company, P1754, lot 44H0121] was mixed with deionized water to produce a 20% (v/v) Tween 80 solution.

Ten milliliters of BRIJ 35 [Sigma Chemical Company, P1254, lot 30K0198] was mixed with deionized water to produce a 20% (v/v) Brij 35 solution.

Polymyxin B, 50 mg, [Sigma P-1004, lot 22H2517] was dissolved in water to produce 40 ml of a Polymyxin B solution, 10,000 U/ml One ml of an overnight culture of *E. coli* cells containing a his-tagged Renilla luciferase fusion protein plasmid was added to 50 ml of fresh L Broth containing tetracycline. The new culture was incubated for four hours at 37C on a shaking incubator at which point 1M IPTG was added to the culture to a final concentration of 1 mM. The culture remained on the shaking incubator for an additional 2½ hours at which point the culture was used in lysis experiments.

1.5 ml microcentrifuge tubes were labeled A through U and B1. The following cell lysis solutions were prepared and aliquoted into the labeled tubes:

| | |
| --- | --- |
| A | 500 ul 4% Triton W30 solution, 250 ul 1 M HEPES pH 7.5, 250 ul nanopure water |
| B | 500 ul 4% DOC solution, 250 ul 1 M HEPES pH 7.5, 250 ul nanopure water |
| C | 500 ul 4% Sodium Docecyl Sulfate solution, 250 ul 1 M HEPES pH 7.5, 250 ul nanopure water |

-continued

| | |
|---|---|
| D | 500 ul 4% Rhodameen VP-532/SPB solution, 250 ul 1 M HEPES pH 7.5, 250 ul nanopure water |
| E | 500 ul 4% Rhodameen PN-430 solution, 250 ul 1 M HEPES pH 7.5, 250 ul nanopure water |
| F | 500 ul 4% Tomah E-14-5 solution, 250 ul 1 M HEPES pH 7.5, 250 ul nanopure water |
| G | 500 ul 4% Tomah E-18-15 solution, 250 ul 1 M HEPES pH 7.5, 250 ul nanopure water |
| H | 500 ul 4% Tomah E-14-2 solution, 250 ul 1 M HEPES pH 7.5, 250 ul nanopure water |
| I | 500 ul 4% Trymeen 6607 solution, 250 ul 1 M HEPES pH 7.5, 250 ul nanopure water |
| J | 100 ul 20% Tween 20 solution, 250 ul 1 M HEPES pH 7.5, 650 ul nanopure water |
| K | 100 ul Polymyxin B solution, 10,000 U/ml, 250 ul 1 M HEPES pH 7.5, 250 ul nanopure water |
| L | As A but 100 ul nanopure water replaced with 100 ul of 10,000 U/ml Polymyxin B |
| M | As B but 100 ul nanopure water replaced with 100 ul of 10,000 U/ml Polymyxin B |
| N | As C but 100 ul nanopure water replaced with 100 ul of 10,000 U/ml Polymyxin B |
| O | As D but 100 ul nanopure water replaced with 100 ul of 10,000 U/ml Polymyxin B |
| P | As E but 100 ul nanopure water replaced with 100 ul of 10,000 U/ml Polymyxin B |
| Q | As F but 100 ul nanopure water replaced with 100 ul of 10,000 U/ml Polymyxin B |
| R | As G but 100 ul nanopure water replaced with 100 ul of 10,000 U/ml Polymyxin B |
| S | As H but 100 ul nanopure water replaced with 100 ul of 10,000 U/ml Polymyxin B |
| T | As I but 100 ul nanopure water replaced with 100 ul of 10,000 U/ml Polymyxin B |
| U | As J but 100 ul nanopure water replaced with 100 ul of 10,000 U/ml Polymyxin B |
| B1 | 250 ul 1 M HEPES pH 7.5, 750 ul nanopure water |

The tubes were closed and vortexed for 5 min. The solutions in tubes C and N appeared turbid after mixing, the solution in tubes H, L and S appeared slightly milky after mixing based on empirical observation.

Fresh 0.5 ml plastic microfuge tubes were labeled A through U and B1 and 50 ul of the solutions in the corresponding 1.5 ml tubes was transferred to the corresponding 0.5 ml tube. Two hundred microliters of bacterial culture described above was added to the 0.5 ml microfuge tubes and the tubes were mixed by vortex for 3 sec. The 0.5 ml tubes were then spun at 12,000 RPM in a microcentrifuge at room temperature for 5 min. The supernatants were transferred to fresh, labeled tubes and the pellets were placed in a −20° C. freezer.

Renilla Luciferase Assay Reagent was made as in Example 2 and 100 ul of the reagent was placed in luminometer tubes. Ten microliters of the supernatants were mixed with 240 ul of 10× Cell Lysis Reagent formulation A prepared in Example 2. Duplicate 5 ul samples of the diluted supernatants were added to luminometer tubes, the luminometer tubes were vortexed for 2 sec and light production was measured using a Turner TD 20/20 Luminometer (Turner Designs, Sunnyvale, Calif.).

After freezing for approximately 30 min at −20° C., 250 ul of the 10× Cell Lysis Reagent formulation A prepared in Example 2 was added to each cell pellet. The cell pellets were then resuspended by vortex treatment approximately 5 sec. Duplicate five microliters of the resuspended pellets was added to luminometer tubes containing 100 ul of the Renilla Luciferase Assay Reagent, the solution mixed 2 sec and the light produced by the solution measured using a Turner TD 20/20 Luminometer. The following relative light unit readings were recorded:

| Sample | Supernatant sample readings | Pellet sample readings |
|---|---|---|
| A | 0.059, 0.029 | 7618, 7369 |
| B | 0.153, 0.093 | 962.3, 1020 |
| C | 0.028, 0.140 | 122.9, 147.8 |
| D | 4.620, 6.625 | 7219, 8008 |
| E | 0.381, 0.414 | 7220, 6757 |
| F | 0.494, 0.293 | 342.4, 412.9 |
| G | 2.587, 2.116 | 6201, 7601 |
| H | 0.026, 0.041 | 1.169, 1.252 |
| I | 11.56, 2.641 | 6665, 7285 |
| J | 29.19, 63.07 | 4205, 4981 |
| K | 2.419, 3.877 | 4148, 6557\ |
| L | 0.096, 0.072 | 6479, 4515 |
| M | 4.611, 26.97 | 77.83, 24.89 |
| N | 6.128, 1.829 | 66.65, 64.44 |
| O | 83.60, 152.0 | 474.2, 214.1 |
| P | 2.535, 2.532 | 8.927, 6.835 |
| Q | 0.133, 0.165 | 1.258, 1.578 |
| R | 144.2, 162.5 | 840.6, 743.6 |
| S | 0.020, 0.035 | 1.442, 1.495 |
| T | 128.6, 123.1 | 1636, 1318 |
| U | 18.52, 30.24 | 4113, 4822 |
| B1 | 0.215, 5.599 | 6995, 6129 |

These results show that some detergent formulations, such as those using SDS with or without Polymyxin B [Solutions C and N], have very low total enzyme activity measurements compared with the no detergent control [Solution B1] or a solution only containing Polymyxin B in buffer [Solution K]. Other solutions, such as those with Tween 20 with or without Polymyxin B [Solutions J and U] retain substantial enzyme activity but have the vast majority of the activity in the cell pellet fractions. However, a select few detergents, such as Tomah E-18-15 [Solution R], release a substantial fraction of the enzyme from the cell in the presence of Polymyxin B and also do not greatly reduce the total enzyme activity measured. However, some of these detergents do not release much enzyme in the absence of Polymyxin B [as exemplified by Tomah E-18-15 Solution G]. Since neither Tomah E-18-15 alone [Solution G], nor Polymyxin B alone [Solution K] release enzyme with substantial activity from the cell, it is surprising that when combined the resulting solution [Solution R] can release substantial amounts of enzyme from the cell and preserve the activity of the enzyme in the media.

Example 4

Testing of Additional Detergents

In this example, additional detergents are tested for their ability to release active His-tagged Renilla Luciferase from *E. coli* under experimental conditions similar to those used in Example 3.

Five hundred microliters of the overnight culture (about 36 hours old) used for generation of the culture used in Example 3 was used to inoculate 50 ml of L Broth+Tet, and this culture was grown at 37° C. with shaking on a shaking incubator for 30 min, at which time 50 ul of 1M isopropyl-beta-D-thiogalactopyranoside (IPTG) was added to the culture and the culture was grown for 2.5 additional hours before being used in the following experiment. The following solutions were made up. Please note that the stock solutions refer to those stock solutions prepared in Example 3:

| Solution | Composition |
|---|---|
| A | 500 ul of Tomah E-18-15 stock solution, 250 ul of 1 M HEPES pH 7.5, 250 ul of nanopure water |
| B | 500 ul of Rhodameen VP-532/SBP stock solution, 250 ul 1 M HEPES pH 7.5, 250 ul of nanopure water |
| C | 500 ul of Trymeen 6607 stock solution, 250 ul of 1 M HEPES pH 7.5, 250 ul of nanopure water |
| D | 100 ul of Tween 20 stock solution, 250 ul of 1 M HEPES pH 7.5, 250 ul of nanopure water |
| E | 100 ul of BRIJ 35 stock solution, 250 ul of 1 M HEPES pH 7.5, 250 ul of nanopure water |
| F | 100 ul of Tergitol NP 9 stock solution 250 ul of 1 M HEPES pH 7.5, 250 ul of nanopure water |
| G | 100 ul of Triton X-100 stock solution, 250 ul of 1 M HEPES pH 7.5, 250 ul of nanopure water |
| H | 100 ul of Polymyxin B stock solution, 250 ul of 1 M HEPES pH 7.5, 250 ul of nanopure water |
| I | 500 ul of Tomah E-18-5 stock solution, 250 ul of 1 M HEPES pH 7.5, 250 ul of nanopure water |
| Con | 250 ul of 1 M HEPES pH 7.5, 750 ul of nanopure water |
| A' | Same as A but nanopure water was reduced by 100 ul and 100 ul of the Polymyxin B stock solution was added. |
| B' | Same as B but nanopure water was reduced by 100 ul and 100 ul of the Polymyxin B stock solution was added. |
| C' | Same as C but nanopure water was reduced by 100 ul and 100 ul of the Polymyxin B stock solution was added. |
| D' | Same as D but nanopure water was reduced by 100 ul and 100 ul of the Polymyxin B stock solution was added. |
| E' | Same as E but nanopure water was reduced by 100 ul and 100 ul of the Polymyxin B stock solution was added. |
| F' | Same as F but nanopure water was reduced by 100 ul and 100 ul of the Polymyxin B stock solution was added. |
| G' | Same as G but nanopure water reduced by 100 ul and 100 ul of the Polymyxin B stock solution was added. |
| I' | Same as I but nanopure water was reduced by 100 ul and 100 ul of the Polymyxin B stock solution was added. |

Thirty-six (36) 1.5 ml plastic microcentrifuge tubes were labeled 1-36 and 100 ul of solution A was added to tubes 1 and 2, 100 ul of solution B added to 3 and 4, and so on, until 100 ul of I' was added to tubes 35 and 36. Four hundred microliters of culture was then added to tubes 1-36 and mixed by inversion 5x, and then the tubes were spun for 4 min at 12,000 RPM in a microcentrifuge at room temperature. Ten microliters of the supernatants in the tubes was added to 290 ul of 50 mM Tris-HCl pH 7.5 and mixed. Five microliters of the diluted supernatants was added to 100 ul of Renilla Luciferase Assay Reagent [see Example 2] in a luminometer tube and light production was measured using a Turner TD 20/20 Luminometer. The following measurements were recorded:

| Tube | Relative Light Units |
|---|---|
| 1 | 45.33 |
| 2 | 35.71 |
| 3 | 61.42 |
| 4 | 66.12 |
| 5 | 45.71 |
| 6 | 41.47 |
| 7 | 1.081 |
| 8 | 1.317 |
| 9 | 3.881 |
| 10 | 4.912 |
| 11 | 14.14 |
| 12 | 8.312 |
| 13 | 11.80 |
| 14 | 14.76 |
| 15 | 7.680 |
| 16 | 3.386 |
| 17 | 87.66 |
| 18 | 67.48 |
| 19 | 0.882 |
| 20 | 0.951 |
| 21 | 1928 |
| 22 | 2382 |
| 23 | 1895 |
| 24 | 1964 |
| 25 | 2130 |
| 26 | 992.0 |
| 27 | 86.11 |
| 28 | 52.57 |
| 29 | 196.0 |
| 30 | 191.0 |
| 31 | 2432 |
| 32 | 2459 |
| 33 | 1545 |
| 34 | 1451 |
| 35 | 2094 |
| 36 | 2327 |

The above data indicates that some detergent formulations can release more cytoplasmic protein from E. coli cells treated in media without Polymyxin B than others. In addition many detergents, when combined with Polymyxin B, release substantially more cytoplasmic protein to media. For example, Tomah E-18-5, Rhodameen VP 532/SPB, Trymeen 6607, and Tomah E-18-15 [tested in tubes 17 and 18, 3 and 4, 5 and 6, and 1 and 2 respectively in the table above] release much more of the cytoplasmic contents of E. coli (as measured by the release of His Renilla Luciferase) than those formulations containing Tween 20, Polymyxin B and buffer, or buffer alone [tested in tubes 7 and 8, 15 and 16, and 19 and 20, respectively]. However, as indicated above, addition of Polymyxin B to some detergents makes the release of the active protein much more effective than using either the detergent alone or Polymyxin B alone. For instance, compare the Relative Light Units of Tomah E-18-5 alone (tubes 17 and 18) and Polymyxin B alone, (tubes 15 and 16) versus Tomah E-18-5 and Polymyxin B, (tubes 35 and 36, respectively). It is also clear from the data above that both ionic detergents (such as Tomah E-18-15) and non-ionic detergents (such as Triton X100) may be effective at releasing protein from E. coli in media when combined with a cell membrane altering compound such as Polymyxin B. This data is represented graphically in FIG. 2A and FIG. 2B.

Example 5

HLB Study of the Release of His-PPE Luciferase from E. Coli

In this example, various detergent solutions with well-known HLB indices are tested for their ability to release thermostable firefly luciferase protein from E. coli cells in combination with Polymyxin B. The E. coli strain was prepared by transforming E. coli with a vector expressing histidine-tagged thermostable firefly luciferase. The vector was constructed by conventional methods. See Maniatis et al., "Molecular Cloning: A Laboratory Manual," 2nd Edition, Cold Spring Harbor Laboratory, Cold Spring Harbor, N.Y. (1982). The HLB index is a measure used by those experienced in the field of surfactant and detergent use and well known texts, such as McCutcheon's 1996, vol 1: Emulsifiers and Detergents (McCutcheon's division Mc Publishing Co., 175 Rock Road, Glen Rock, N.J.) contain listings of the detergents and their HLB value. When the values of the HLB detergents that were effective in releasing protein in the presence of Polymyxin B from examples 3 and 4 above were examined, it was noted that these detergents had HLB values between and including 11 to 16 while those that were ineffective in releasing protein or which may have inactivated the protein had values either below 11 or above 16. In this study in particular, a series of detergents known as Tergitols available from Union Carbide (Danbury, Conn.) were used to determine an effective HLB range since these detergents had a wide range of HLB indices. By using this series of detergents we were able to determine if these materials displayed the same HLB index dependence on protein release seen with other detergents. It was believed that HLB index dependence on protein release could be confirmed by using the Tergitol series of detergents since the detergents in the series have essentially the same chemical structure. In other words, if we could demonstrate that Tergitol solutions made from detergents having HLB values between or at 11-16 effectively released protein in combination with Polymyxin B but those outside this range did not, the results would verify that detergents within the HLB range of 11-16 would effectively release active proteins or peptides from cells.

50 ml of L Broth+Tet was inoculated with an *E. coli* strain expressing His-PPE-Luciferase and grown overnight at 37C on a shaking incubator. After overnight growth, 0.5 ml of the culture was diluted into 50 ml of fresh L Broth+Tet in a 250 ml flask and grown at 37° C. with shaking until it reached a density of OD600 of 0.6. At that point, 1M IPTG was added to a final concentration of 1 mM and the culture was incubated for an additional 6 hrs before use in the following experiment.

The following stock solutions were prepared:
Three ml of Tergitol NP-4 (Sigma Chemical Co. NP-4 lot 52K1286) was dissolved in deionized water to 30 ml.
Three ml of Tergitol NP-7 (Sigma Chemical Co. NP-7 lot 79H0109) was dissolved in deionized water to 30 ml.
Three ml of Tergitol NP-9 (Sigma Chemical Co. NP-8 lot 41K0156) was dissolved in deionized water to 30 ml.
Three ml of Tergitol NP-10 (Sigma Chemical Co. NP-10 lot 78H1091) was dissolved in deionized water to 30 ml.
Three grams of Tergitol NP-40 (Sigma Chemical Co. NP-40 lot 110K0225) was dissolved in deionized water to 30 ml.
Three ml of Tergitol 15-S-5 (Sigma Chemical Co. 15-S-5 lot 61K0040 was dissolved in deionized water to 30 ml.
Three ml of Tergitol 15-S-12 (Sigma Chemical Co. 15-S-12 lot 81K0292) was dissolved in deionized water to 30 ml.
Three grams of Tergitol 15-S-30 (Sigma Chemical Co. 15-S-30 lot 20H0123) was dissolved in deionized water to 30 ml.

The following solutions were assembled:

| Solution | Composition |
| --- | --- |
| T1 | 100 ul of Tergitol NP-4 stock solution, 500 ul HEPES pH 7.5, 400 ul of nanopure water |
| T2 | 100 ul of Tergitol NP-7 stock solution, 500 ul HEPES pH 7.5, 400 ul of nanopure water |
| T3 | 100 ul of Tergitol NP-9 stock solution 500 ul HEPES pH 7.5, 400 ul of nanopure water |
| T4 | 100 ul of Tergitol NP-10 stock solution, 500 ul HEPES pH 7.5, 400 ul of nanopure water |
| T5 | 100 ul of Tergitol NP-40 stock solution, 500 ul HEPES pH 7.5, 400 ul of nanopure water |
| T6 | 100 ul of Tergitol 15-S-5 stock solution, 500 ul HEPES pH 7.5, 400 ul of nanopure water |
| T7 | 100 ul of Tergitol 15-S-12 stock solution, 500 ul HEPES pH 7.5, 400 ul of nanopure water |
| T8 | 100 ul of Tergitol 15-S-30 stock solution, 500 ul HEPES pH 7.5, 400 ul of nanopure water |
| TP1 | as T1 but 100 ul of Polymyxin B stock solution of Example 3 replaces 100 ul of nanopure water |
| TP2 | as T2 but 100 ul of Polymyxin B stock solution of Example 3 replaces 100 ul of nanopure water |
| TP3 | as T3 but 100 ul of Polymyxin B stock solution of Example 3 replaces 100 ul of nanopure water |
| TP4 | as T4 but 100 ul of Polymyxin B stock solution of Example 3 replaces 100 ul of nanopure water |
| TP5 | as T5 but 100 ul of Polymyxin B stock solution of Example 3 replaces 100 ul of nanopure water |
| TP6 | as T6 but 100 ul of Polymyxin B stock solution of Example 3 replaces 100 ul of nanopure water |
| TP7 | as T7 but 100 ul of Polymyxin B stock solution of Example 3 replaces 100 ul of nanopure water |
| TP8 | as T8 but 100 ul of Polymyxin B stock solution of Example 3 replaces 100 ul of nanopure water |
| Tcon | 500 ul of HEPES pH 7.5, 500 ul nanopure water |
| TO-1 | 250 ul of Tomah E-18-15 stock solution of Example 3, 500 ul of HEPES pH 7.5, 250 ul of nanopure water |
| TOP-1 | as TO-1 but 100 ul of Polymyxin B stock solution of Example 3 replaces 100 ul of nanopure water |
| TO-2 | 250 ul of Tomah E-18-5 solution prepared in Example 3 500 ul of HEPES pH 7.5, 250 ul of nanopure water. |
| TOP-2 | as TO-2 but 100 ul of Polymyxin B stock solution of Example 3 replaces 100 ul of nanopure water |

Forty-two 1.5 ml plastic microcentrifuge tubes were numbered 1-42 and 200 ul of the above solutions were added to the tubes as indicated below.

| Tube | Solution | Tube | Solution | Tube | Solution |
| --- | --- | --- | --- | --- | --- |
| 1&2 | T1 | 3&4 | T2 | 5&6 | T3 |
| 7&8 | T4 | 9&10 | T5 | 11&12 | T6 |
| 13&14 | T7 | 15&16 | T8 | 17&18 | TO-1 |
| 19&20 | TO-2 | 21&22 | TP1 | 23&24 | TP2 |
| 25&26 | TP3 | 27&28 | TP4 | 29&30 | TP5 |
| 31&32 | TP6 | 33&34 | TP7 | 35&36 | TP8 |
| 37&38 | TOP-1 | 39&40 | TOP-2 | 41&42 | Tcon |

Eight hundred microliters of bacterial culture was added to the tubes and the resulting solutions mixed. The tubes were spun at 12,000 RPM for 4 min at room temperature and the supernatants transferred to fresh tubes. The pellets were resuspended in a solution containing 0.2% [v/v] Triton X-100, 0.2% Tomah E-18-15, and 200 U/ml of Polymyxin B in 100 mM HEPES pH 7.5 [Triton, Tomah and Polymyxin B stock solutions used are described in Example 3; HEPES pH 7.5 was diluted from a 1M stock]. Both the supernatant samples and the resuspended cell pellets were diluted at a rate of 1 part sample to 19 part into 1% Triton X-100, the solutions mixed and 4 ul of the resulting solutions were added to 100 ul of Luciferase Assay Reagent (LAR), (made by dissolving Luciferase Assay Substrate, Promega Corp E151A with Luciferase Assay Buffer, Promega Corp. E152A as described by the manufacturer) in a luminometer tube. Immediately after addition, the tube was read immediately using a Turner TD 20/20 Luminometer. The following measurements were made.

|  | Relative Light Units | | | Relative Light Units | |
|---|---|---|---|---|---|
|  | | | | Pellet | Media |
| Sample | Pellet sample | Media sample | Sample | Sample | Sample |
| Tube 1 | 6377 | 52.81 | Tube 2 | 5546 | 41.91 |
| Tube 3 | 2551 | 68.38 | Tube 4 | 5829 | 63.13 |
| Tube 5 | 4525 | 54.53 | Tube 6 | 6277 | 67.64 |
| Tube 7 | 5571 | 61.88 | Tube 8 | 4014 | 64.06 |
| Tube 9 | 5582 | 45.83 | Tube 10 | 4896 | 39.33 |
| Tube 11 | 4602 | 46.21 | Tube 12 | 4786 | 50.63 |
| Tube 13 | 4583 | 52.63 | Tube 14 | 4359 | 43.93 |
| Tube 15 | 3888 | 42.73 | Tube 16 | 5487 | 45.90 |
| Tube 17 | 4954 | 73.98 | Tube 18 | 5097 | 166.3 |
| Tube 19 | 563.0 | 93.70 | Tube 20 | 1681 | 107.0 |
| Tube 21 | 895.0 | 83.48 | Tube 22 | 1227 | 85.40 |
| Tube 23 | 272.7 | 5423 | Tube 24 | 215.2 | 5751 |
| Tube 25 | 155.5 | 8922 | Tube 26 | 175.4 | 6299 |
| Tube 27 | 159.3 | 6773 | Tube 28 | 187.4 | 6794 |
| Tube 29 | 2133 | 203.2 | Tube 30 | 2744 | 281.8 |
| Tube 31 | 5069 | 476.9 | Tube 32 | 5741 | 177.3 |
| Tube 33 | 229.9 | 5857 | Tube 34 | 232.3 | 7088 |
| Tube 35 | 2299 | 174.8 | Tube 36 | 2621 | 262.8 |
| Tube 37 | 331.7 | 7669 | Tube 38 | 195.8 | 8094 |
| Tube 39 | 156.1 | 6816 | Tube 40 | 172.2 | 8842 |
| Tube 41 | 5219 | 60.97 | Tube 42 | 5279 | 53.64 |

These results indicate that none of the Tergitol solutions tested were able to release the majority of the His-PPE-Luciferase by themselves but that some of them do release the majority of the enzyme when combined with Polymyxin B (for example, compare Tergitol NP-7 [tubes 3&4] without Polymyxin B, to tubes 23&24 with Polymyxin B] see also tubes 37 and 38 where approximately 95% of the enzyme activity measured is in the cell supernatant) while other Tergitol solutions are ineffective in releasing the enzyme even in the presence of Polymyxin B (for example, compare Tergitol NP-40 [tubes 15&16] without Polymyxin B, to tubes 35&36 with Polymyxin B]).

The McCutcheon's reference above indicates that these detergents have the following HLB indices: Tergitol 15-S-30, 8.0; Tergitol NP-4, 8.9; Tergitol 15-S-5, 10.5; Tergitol NP-7, 11.7; Tergitol NP-9, 12.9; Tergitol NP-10, 13.6; Tergitol 15-S-12, 14.5; Tergitol NP-40, 17.8.

When this information is combined with the results above, one can see that Tergitol solutions made and tested as above with an HLB index below 11 or above 16 are ineffective in releasing protein to the media from *E. coli* cells while those between or at 11 to 16 are effective in releasing protein to the media. These results then do indicate that detergents with HLB values between HLB 11-16, when formulated with Polymyxin B as above, would be expected to release protein into media from *E. coli* cells grown as above. These results are presented graphically in FIG. 3.

Example 6

Measurement of the Release of β-Galactosidase from *E. coli* Treated in Media With a Detergent/Polymyxin B Solution is Followed Over Time In this example, the release of *E. coli* beta-galactosidase, a protein tetramer with an apparent molecular weight for the active tetramer of approximately 460,000 daltons, will be followed over time.

An overnight culture of *E. coli* strain W3110 (obtained from the CGSC: *E. coli* Genetic Stock Center at Yale University) was grown overnight at 37C in L Broth in a shaking incubator. After overnight growth, the culture was diluted into fresh L Broth 1:100 and grown at 37° C. until the density of the culture reached OD600 of 0.6, then 1M IPTG was added to a final concentration of 1 mM and the culture grown for 4 additional hours before use in the study below.

The following solution, which will be referred to as 10× Cell Lysis Reagent, was made by mixing: 25 ml of 1M HEPES, pH 7.5; 5 ml of Triton X 100 (Sigma Chemical Corp. T9284, lot 118H0297); 2 ml of Tomah E-18-15 (Tomah Chemical Company); 25 mg of Polymyxin B (Sigma Chemical Co. P-1004, 22K2517) and diluting the solution to 50 ml with nanopure water.

100 ul of 10× Cell Lysis Reagent was added to five 1.5 ml plastic microcentrifuge tubes labeled 1, 3, 5, 7, and 9 and 100 ul of nanopure water was added to a sixth tube labeled 0. 900 ul of the W3110 culture was added to tubes 0, 1, 3, 5, 7 and 9. Tubes 0 and 1 were mixed by inversion and immediately centrifuged at 14,000 RPM for 2 min at 4° C. The remaining tubes were mixed by inversion and a timer started. Tube 3 was centrifuged as above at 5 min; tube 5 at 15 min post mixing; tube 7 at 25 min and tubes 9 at 30 min post mixing. The supernatants were transferred to fresh tubes and the pellets, when present, were resuspended in 1 ml of 1× Cell Lysis Reagent [made by dilution of 1 part 10× Cell Lysis Reagent with 9 parts nanopure water].

Fifty microliters of the supernatants and resuspended cell pellets were diluted with 950 ul of 20 mM Tris-HCl pH 7.3 to produce diluted samples.

Five ml of Assay Buffer, 2× (from Promega Kit E2000 B)-) diluted with 5 ml of nanopure water and 200 ul placed in the wells of a clear microtiter plate. Five microliters of the diluted samples were added to two separate wells of the microtiter plate and a timer started. When some of the wells began to show yellow color by visual observation, the absorbance of the solution at 420 nm was read on a microtiter plate reader. The values recorded were:

| Tube # | Solution and Time | OD405, Well 1 | OD405, Well 2 | Avg* |
|---|---|---|---|---|
| 0 | No Detergent Treatment, 0 Min, Pellet | 0.507 | 0.529 | 0.466 |
| 0 | No Detergent Treatment, 0 Min, Sup | 0.056 | 0.051 | 0.0015 |
| 1 | Detergent, 0 min, Pellet | 0.465 | 0.451 | 0.406 |
| 1 | Detergent, 0 min, Sup | 0.066 | 0.071 | 0.0165 |
| 3 | Detergent, 5 min, Pellet | 0.511 | 0.483 | 0.445 |
| 3 | Detergent, 5 min, Sup | 0.071 | 0.064 | 0.0155 |
| 5 | Detergent, 15 min, Pellet | 0.496 | 0.453 | 0.4225 |
| 5 | Detergent, 15 min, Sup | 0.059 | 0.057 | 0.006 |
| 7 | Detergent, 25 min, Pellet | 0.456 | 0.503 | 0.4275 |
| 7 | Detergent, 25 min, Sup | 0.057 | 0.057 | 0.005 |
| 9 | Detergent, 30 min, Pellet | 0.586 | 0.604 | 0.543 |
| 9 | Detergent, 30 min, Sup | 0.056 | 0.059 | 0.0055 |

*Avg. represents the net average RLU (average RLU of cell culture sample (treated or untreated) minus the average RLU of reagent sample not containing cell culture (Average 0.052 RLU).

This data indicates that under these conditions, a low amount of beta-galactosidase protein was released into the media. This protein is very large in size and is a tetramer of subunits of approximately 115,000 daltons, giving a size for the active protein of 460,000 daltons.

In order to increase the amounts of beta-galactosidase protein released into media, the 1× Cell lysis reagent containing lysozyme of Example 1(c) was utilized.

*E. coli* cells (*E. coli* JM109 or *E. coli* BL21(DE3)pLysS bacterial strains, L2001 and L1191 respectively, Promega Corporation, Madison Wis.) capable of separately expressing the his-tagged proteins ribonuclease inhibitor RNasin, RNaseHI, methionyl tRNA synthetase, thermostable firefly luciferase, β-galactosidase, and humanized Renilla luciferase were incubated overnight in L broth and appropriate antibiotics. Five microliters of the overnight cultures were transferred to 250 ml flasks containing 50 ml L broth and appropriate antibiotics, the bacterial cells were grown to OD600 of 0.4-0.8, and protein expression was induced with IPTG at 1 mM final concentration. Cell cultures were allowed to grow post-induction overnight at 25° C. Following the second night of incubation, bacterial culture ODs were now between 1.8-3.4. One milliliter of each culture was transferred to wells of a deepwell cell culture plate with 6 columns. Each column was dispensed with one type of bacterial culture; column 1 contained cells with his-RNaseHI, column 2 contained cells with his-humanized Renilla luciferase, column 3 contained cells with his-RNasin, column 4 contained cells with his-thermostable firefly luciferase, column 5 contained cells with his-MGH, and column 6 contained cells with his-β-galactosidase. The plate was centrifuged and the supernatants were removed. Row A samples received 200 ul of cell lysis reagent and served as the control wells, whereas Row B samples received 200 ul of cell lysis reagent with 1 mg/ml lysozyme. Protein purification was performed on the BioMek 2000 using the Magne-His™ Protein Purification System (Catalog number V8500, Promega Corporation, Madison Wis.)

Following protein purification on the BioMek 2000, 20 ul of each purified protein sample was visualized using SDS-PAGE. As seen in FIG. 12, the lanes at the top of the gels correspond to; M=molecular weight marker, 1=his-RNaseHI, 2=his-humanized Renilla luciferase, 3=his-RNasin, 4=his-thermostable firefly luciferase, 5=his-methionyl tRNA synthetase, and 6=his-β-galactosidase. FIG. 12 demonstrates that, compared to the negative control gel (-lysozyme), the addition of lysozyme to the cell lysis reagent enhanced the amount of protein captured and purified for his-β-galactosidase, the largest of the test proteins.

Example 7

Reaction Time Study of the Release of GST-Firefly-Luciferase from E. coli Treated in Media With a Detergent/Polymyxin B Solution In this example, the release of a glutathione S-transferase (GST)-labeled firefly luciferase protein of approximately 90,000 daltons (GST-PPE-Luc) from E. coli cells will be followed over time. The E. coli strain was prepared by transforming E. coli with a vector expressing GST-tagged firefly luciferase. The vector was constructed by conventional methods. See Maniatis et al., "Molecular Cloning: A Laboratory Manual," $2^{nd}$ Edition, Cold Spring Harbor Laboratory, Cold Spring Harbor, N.Y. (1982). Cells were grown as in Example 6 except that a strain of E. coli expressing a fusion of GST and PPE Luciferase was grown and L Broth+Tet was used as growth media.

Tubes were labeled and manipulated as in Example 6. Samples from both the supernatant and cell pellets for each tube were added to LAR as in Example 5, except in this experiment only single readings were taken. The following values were recorded:

| Detergent Treatment Time (min) | Relative Light Units Pellet | | % Activity in |
|---|---|---|---|
| 0 | 221 | 141 | 39.0 |
| 5 | 250 | 128 | 33.9 |
| 15 | 142.7 | 133 | 48.2 |
| 25 | 164.1 | 175.9 | 51.7 |
| 35 | 191 | 168 | 46.8 |

The "% Activity" noted in the above table (and other examples) refers to the % of RLU measured in the supernatant versus the total RLU measured (supernatant plus pellet). The above data indicate that this protein, approximately 90,000 daltons in size, is released from cells in media to a significant extent by application of the cell lysis reagent of the present invention under these reaction conditions.

Example 8

Measurement of Release of GST Renilla Luciferase from E. coli Treated in Media With a Detergent/Polymyxin B Solution is Followed Over Time In this example, the release of a protein of approximately 60,000 daltons (GST-Renilla Luciferase) from E. coli cells will be followed over time. The E. coli strain was prepared by transforming E. coli with a vector expressing GST-tagged Renilla luciferase. The vector was constructed by conventional methods. See Maniatis et al., "Molecular Cloning: A Laboratory Manual," $2^{nd}$ Edition, Cold Spring Harbor Laboratory, Cold Spring Harbor, N.Y. (1982).

Cells were grown as in Example 6 except that a strain of E. coli expressing a fusion of GST and Renilla Luciferase was grown and L Broth+Tet was used as growth media.

Tubes were labeled and manipulated as in example 6 and the media and pellet samples sampled and the samples were added to LAR [described in Example 5] except in this experiment only single readings were taken. The following values were recorded:

| Detergent Treatment Time (min) | Relative Light Units Pellet | Supernate | % Activity in Supernate |
|---|---|---|---|
| 0 | 23 | 72 | 75.8 |
| 5 | 13 | 95 | 88.0 |
| 15 | 3 | 111 | 97.4 |
| 25 | 10.5 | 98.9 | 90.4 |
| 35 | 10.4 | 104.6 | 91.0 |

The above data indicates that this protein, approximately 60,000 daltons in size, is substantially released from cells in media by application of a Cell Lysis Reagent of the present invention under these conditions.

Example 9

Effectiveness of Detergents at Various Concentrations

In this example, the ability of various detergents to release His-tagged Renilla luciferase protein from E. coli cells in the presence of Polymyxin B is measured at various detergent concentrations. An *E. coli* culture was grown as described in Example 4. The following solutions were created. Please note that the stock solutions refer to those prepared in Example 3:

| Solution | Composition |
| --- | --- |
| AH | 100 ul of Triton X-100 stock solution, 250 ul of HEPES pH 7.5, 100 ul of Polymyxin B stock solution, 550 ul of nanopure water; |
| AM | 10 ul of Triton X-100 stock solution, 250 ul of HEPES pH 7.5, 100 ul of Polymyxin B stock solution, 640 ul nanopure water; |
| AL | 1 ul of Triton X-100 stock solution, 250 ul of HEPES pH 7.5, 100 ul of Polymyxin B stock solution, 649 ul of nanopure water; |
| BH | 100 ul of Tergitol NP-9 stock solution, 250 ul of HEPES pH 7.5, 100 ul of Polymyxin B stock solution, 550 ul of nanopure water; |
| BM | 10 ul of Tergitol NP-9 stock solution, 250 ul of HEPES pH 7.5, 100 ul of Polymyxin B stock solution, 640 ul nanopure water; |
| BL | 1 ul of Tergitol NP-9 stock solution, 250 ul of HEPES pH 7.5, 100 ul of Polymyxin B stock solution, 649 ul of nanopure water; |
| CH | 500 ul of Tomah E-18-15 stock solution, 250 ul of HEPES pH 7.5, 100 ul of Polymyxin B stock solution, 150 ul of nanopure water; |
| CM | 50 ul of Tomah E-18-15 stock solution, 250 ul of HEPES pH 7.5, 100 ul of Polymyxin B stock solution, 600 ul nanopure water; |
| CL | 5 ul of Tomah E-18-15 stock solution, 250 ul of HEPES pH 7.5, 100 ul of Polymyxin B stock solution, 645 ul of nanopure water; |
| DH | 500 ul of Rhodameen VP-523/SPB stock solution, 250 ul of HEPES pH 7.5, 100 ul of Polymyxin B stock solution, 150 ul of nanopure water; |
| DM | 50 ul of Rhodameen VP-523/SPB stock solution, 250 ul of HEPES pH 7.5, 100 ul of Polymyxin B stock solution, 600 ul nanopure water; |
| DL | 5 ul of Rhodameen VP523/SPB stock solution, 250 ul of HEPES pH 7.5, 100 ul of Polymyxin B stock solution, 645 ul of nanopure water; |
| EH | 500 ul of Trymeen 6607 stock solution, 250 ul of HEPES pH 7.5, 100 ul of Polymyxin B stock solution, 150 ul of nanopure water; |
| EM | 50 ul of Trymeen 6607 stock solution, 250 ul of HEPES pH 7.5, 100 ul of Polymyxin B stock solution, 600 ul nanopure water; |
| EL | 5 ul of Trymeen 6607 stock solution, 250 ul of HEPES pH 7.5, 100 ul of Polymyxin B stock solution, 645 ul of nanopure water; |
| FH | 500 ul of Tomah E-18-5 stock solution, 250 ul of HEPES pH 7.5, 100 ul of Polymyxin B stock solution [prepared in Example 3], 150 ul of nanopure water; |
| FM | 50 ul of Tomah E-18-5 stock solution, 250 ul of HEPES pH 7.5, 100 ul of Polymyxin B stock solution, 600 ul nanopure water; |
| FL | 5 ul of Tomah E-18-5 stock solution, 250 ul of HEPES pH 7.5, 100 ul of Polymyxin B stock solution, 645 ul of nanopure water; |
| Con 1 | 250 ul of HEPES pH 7.5, 650 ul of nanopure water, 100 ul of Polymyxin B stock solution; |
| Con 2 | 250 ul of HEPES pH 7.5, 750 ul of nanopure water. |

100 ul of each of the above solutions above was aliquoted into 20 1.5 ml microcentrifuge tubes, and then 400 ul of bacterial culture was added. The tubes were closed and mixed by inversion five (5) times, and spun at 13,000 RPM for 4 min at room temperature. The supernatants were removed to fresh tubes and a 10 ul sample of each supernatant was diluted into 290 ul of 50 mM Tris-HCl pH 7.5, and 5 ul of the diluted sample was added to 100 ul of Renilla Luciferase Assay Reagent [from the stock solution prepared in Example 2] in a luminometer tube, mixed by vortex treatment and light production measured immediately using a Turner TD 20/20 luminometer. The relative light unit values measured were as follows:

| Sample Tested | Rel. Light Units |
| --- | --- |
| AH | 780.7 |
| AM | 412.5 |
| AL | 1.332 |
| BH | 510.6 |
| BM | 539.9 |
| BL | 5.870 |
| CH | 742.2 |
| CM | 286.0 |
| CL | 514.2 |
| Con 1 | 0.926 |
| DH | 702.6 |
| DM | 328.1 |
| DL | 6.931 |
| EH | 1655 |
| EM | 388.7 |
| EL | 125.9 |
| FH | 1005 |
| FM | 574.9 |
| FL | 391.4 |
| Con 2 | 0.228 |

As can be seen, some detergents, in combination with Polymyxin B can release significant amounts of protein from *E. coli* in media even at concentrations much lower than those used in earlier examples. For instance, Tomah E-18-15, in formulation CH is similar in concentration to that used in earlier examples and released 742.2 RLUs of activity under these conditions. This same detergent in formulation CL released almost the same amount of activity [514.2 RLUs] even though it is present in only 1% the concentration as used in formulation CH. This data is also presented in a graphical form in FIG. 4. Therefore, some detergents are effective in releasing enzyme even at very low concentrations.

In order to confirm that some detergents are more effective in releasing protein at very low concentrations when supplemented with Polymyxin B, 20 additional 1.5 ml tubes were numbered 1-20. Tubes 1-3 were given 100 ul of AL; tubes 4-6, 100 ul of BL; tubes 7-9, 100 ul CL; tubes 10-12, 100 ul DL; tubes 13-15, 100 ul EL; tubes 16-18, 100 ul FL, tube 19, 100 ul Con1, tube 20,100 ul Con2. Four hundred microliters of the aforementioned culture was added to tubes 1-20, the tubes were capped and mixed by inversion 5 times, spun at 12,000 RPM for 5 min at room temperature, and the supernatants removed to fresh tubes. The pellet samples were resuspended in 1× Cell Lysis Reagent prepared in Example 2. Since no pellets were visible in tubes 16-18, the 1× Cell Lysis Reagent was not added to these tubes, and no cell pellet sample was therefore available from these tubes. The supernatant samples and the resuspended cell pellet samples were diluted 1:30 into 1× Cell Lysis Reagent, mixed by vortex treatment, then 5 ul of the material was added to 100 ul of Renilla Luciferase Assay Solution in a luminometer tube and light production measured immediately using a Turner TD 20/20 luminometer. The following Relative Light Unit readings were recorded:

| Tube | Detergent | Relative Light Units In Supernatant sample | Relative Light Units in cell pellet sample |
| --- | --- | --- | --- |
| 1 | Triton X-100 | 14.83 | 1941 |
| 2 | " | 11.66 | 1973 |
| 3 | " | 8.058 | 1562 |
| 4 | Tergitol NP-9 | 29.69 | 1498 |

-continued

| Tube | Detergent | Relative Light Units In Supernatant sample | Relative Light Units in cell pellet sample |
|---|---|---|---|
| 5 | " | 28.73 | 1953 |
| 6 | " | 26.52 | 1085 |
| 7 | Tomah E-18-15 | 1713 | 300 |
| 8 | " | 1739 | 296.5 |
| 9 | " | 2130 | 236.7 |
| 10 | Rhodameen VP523 | 28.01 | 2195 |
| 11 | " | 30.47 | 2081 |
| 12 | " | 35.03 | 1115 |
| 13 | Trymeen 6607 | 467.3 | 1248 |
| 14 | " | 359.7 | 1349 |
| 15 | " | 437.7 | 1087 |
| 16 | Tomah E-18-5 | 2049 | na |
| 17 | " | 2137 | na |
| 18 | " | 2224 | na |
| 19 | [buffer alone] | 9.286 | 1982 |
| 20 | [buffer + Polymyxin B] | 9.006 | 2085 |

From these results, it is clear that some materials, such as Tomah E-18-15 and Tomah E-18-5, are surprisingly effective in releasing protein from *E. coli* in media at very low concentrations when combined with Polymyxin B.

Example 10

Purification of Protein Released into Media Using Various Formats

In this example, purification of protein released into culture media by two detergents is attempted on an affinity resin. The results indicate that while a variety of detergents may release protein into media, not every detergent may be equally advantageous for downstream applications.

An *E. coli* culture expressing His-tagged Renilla Luciferase was grown as indicated in Example 3 with the alteration that the culture used in this study was 3 hours post-IPTG induction. After growth, the culture was split into 3-50 ml plastic tubes; 10 ml was placed in a tube labeled CON; 20 ml into a tube labeled TRA-15 and 20 ml into a tube labeled TRA-5. The following solutions were made:

Solution T-5

5 ml of 1M HEPES, pH 7.5, 100 ul of 10,000 U/ml of Polymyxin B [prepared in Example 3], 0.5 ml of a 4% solution of Tomah E-18-5 [prepared in Example 3] and 3.5 ml on nanopure water was combined and mixed.

Solution T-15

Made as T-5 except that 0.5 ml of a 4% solution of Tomah E-18-15 [prepared in Example 3] replaced the Tomah E-18-5 used.

2.5 ml of a five hundred mM HEPES, pH 7.5, buffer was added to the CON tube, 5 ml of T-5 to the TRA-5 tube and 5 ml of T-15 to the TRA-15 tube. The tubes were capped and swirled for 2 min at room temperature. Duplicate 1 ml samples of the three tubes were transferred to a 1.5 ml plastic microcentrifuge tubes and the tubes were spun at 12,000 RPM for 4 min at room temperature. Ten microliters of both the supernatants in the spun and un-spun tubes was diluted with 190 ul of 1× Cell Lysis Reagent prepared in Example 2. After vortex mixing for 1 sec, 5 ul of each sample was added to 100 ul of Renilla Luciferase Assay Solution and light production measured using a Turner TD 20/20 luminometer. The following readings were recorded:

| Sample | Relative light unit reading For Un-spun sample | Relative Light Unit Reading for the duplicate Supernatant sample |
|---|---|---|
| CON | 2250 | 1.206, 1.210 |
| TRA-15 | 2176 | 1468, 1444 |
| TRA-5 | 1401 | 1412, 1408 |

Six 1.5 ml plastic microcentrifuge tubes were labeled T-15 A thru C and T-5 A thru C. One ml samples of the solution in the tube labeled TRA-15 was placed in T-15 A thru C and 1 ml samples of the solution in the tube labeled TRA-5 was placed in T-5 A thru C. Thirty microliters of a 10% (w/v) suspension of magnetic silica resin charged with nickel (prepared in accordance with U.S. patent application No. 60/419,614, filed Oct. 18, 2002, entitled "Compositions and Methods of Separating Molecules" [Atty docket no. B0174893], which is incorporated by reference in its entirety) was added to T-15B and T-5B and 100 ul of the resin was added to T-15C and T-5 C. The solutions were mixed by inversion approximately every 30 seconds. At 5, 10, 15, and 20 minutes post resin addition, the resins were pelleted magnetically and 10 ul samples of the supernatants were diluted into 190 ul of 1× Cell Lysis Reagent, the tubes were then resealed and mixed by inversion approximately every 30 seconds until the final sample was taken at 20 minutes.

Ten microliters of the diluted samples from each time point was added to 100 ul of Renilla Luciferase Assay solution in a luminometer tube, the tube was mixed by 1 sec vortex treatment and light production measured immediately using a Turner TD 20/20 luminometer. The following results were obtained:

| Sample | 5 min | 10 min | 15 min | 20 min |
|---|---|---|---|---|
| 5A | 1254 | 1286 | 1141 | 1045 |
| 5B | 923.9 | 989.6 | 700.4 | 705.3 |
| 5C | 445.2 | 291.1 | 207.8 | 197.4 |
| 15A | 1466 | 1230 | 1404 | 1136 |
| 15B | 520.5 | 331.1 | 294.9 | 260.7 |
| 15C | 174.5 | 118.1 | 98.08 | 91.75 |

This data confirms that (1) the enzymatic activity for proteins released into the media can be preserved when extracting proteins with the cell lysis reagent of the present invention and isolating those proteins with an affinity resin, and (2) increasing the amount of resin used to capture the enzyme also increases the amount of protein captured by the resin.

After the measurement at the 20 min time point was taken, the supernatants in 5B, 5C, 15B and 15C were removed to fresh tubes labeled "unbound" and saved for later assay. The resin pellets were resuspended in 1 ml of 100 mM HEPES pH 7.5 then re-pelleted magnetically. The supernatants were transferred to a labeled tube designated "wash #1" and saved for later assay. A second 1 ml of 100 mM HEPES pH 7.5 was used to resuspend each resin pellet from after wash #1 and the sample repelleted. The supernatant from each tube was transferred to a fresh tube designated "wash #2" and saved for later assay. Five hundred microliters of 500 mM imidazole in 100 mM HEPES pH 7.5 was used to resuspend the resin particles from wash #2, and the solution was allowed to remain with the particles for 2 minutes at room temperature. The resins were then pelleted magnetically and the supernatants removed and placed into a fresh tube labeled "eluted protein". Ten microliter aliquots of the various samples generated during these manipulations were diluted into 190 ul of 1× Cell Lysis Reagent and 5 ul of the diluted material was added to 100 ul of Renilla Luciferase Assay Solution in a luminometer tube, the tube was mixed by vortex treatment 1 sec and light production was measured using a Turner TD 20/20 Luminometer. The following readings were recorded from these samples.

| Sample | Unbound | Wash 1 | Wash 2 | Eluted |
|--------|---------|--------|--------|--------|
| 5B     | 705.3   | 17.45  | 2.84   | 5.9    |
| 5C     | 197.4   | 4.263  | 1.162  | 16.5   |
| 15B    | 260.7   | 160.1  | 65.77  | 1544.0 |
| 15C    | 91.75   | 42.86  | 14.46  | 2270.0 |
| Volume | 1 ml    | 1 ml   | 0.5 ml | 0.5 ml |

This data indicates that the active protein that was captured onto the resin primarily remains on the resin during washing. However, whereas the active protein from the Tomah E-18-15 treated culture can be readily eluted from the resin (yielding 1544 and 2270 relative light units), the proteins released with Tomah E-18-5 treated culture are not readily eluted from the resin under these elution conditions (producing 5.9 and 16.5 relative light units when assayed in an equivalent manner as the Tomah E-18-15 treated culture).

Example 11

High Throughput Purification of Released Protein Using Detergent/Polymyxin B Solutions Made With Detergents at Various HLB Values This example demonstrates the purification of released His-tagged PPE firefly luciferase protein from detergent solutions with a range of HLB indices. The materials used are described in detail in Example 5. This experiment begins with the use of the supernatant samples isolated from detergent Polymyxin B combinations described in Example 5.

Two 200 ul aliquots of the supernatants from the Cell Lysis Reagents identified as TP2, TP3, TP4, TP7, TOP-1 and TOP-2 in Example 5 were placed into individual labeled tubes: TP2, TP3, TP4, TP7, TOP-1 and TOP-2. Fifty ul of magnetic silica resin chelated with nickel [as identified in Example 10] (10% w/v) was added to each of the tubes and the tubes were mixed by inversion. The tubes were allowed to incubate at room temperature for 30 min with occasional inversion, then the resins were pelleted magnetically and the supernatants removed. One hundred and fifty microliters of 100 mM HEPES, pH 7.5 was used to resuspend the resin and the resuspended materials were transferred to row A of a KingFisher™ 96 well plate [Thermo Labsystems Oy, Helsinki, Finland, Cat#97002080, lot 213500]. The following additions were made to the indicated rows of this plate: row B, 150 ul of 100 mM HEPES, pH 7.5; row C, 100 mM NaCl in 100 mM HEPES, pH 7.5; Rows D and E, 150 ul of 500 mM imidazole in 100 mM HEPES, pH 7.5. The plate was then processed on a KingFisher™ magnetic particle processor [Thermo Labsystems, Helsinki, Finland, Product no. 5400000], using the disposable materials recommended by the manufacturer. The liquids were mixed for several seconds in the initial well according to the robotic program. The magnetic resin was then collected and transferred to the next row of wells so that the particles proceeded from row A to B, C, D and finally E, then were removed from E and the robot continued to move the particles to the remaining wells. After the plate was processed, 10 ul of the unbound material in the original supernatant tubes provided with magnetic silica was diluted with 190 ul of 1× Cell Lysis Reagent. Samples in row D of the KingFisher plate were diluted 1:10 consecutively with 1× Cell Lysis Reagent. After dilution, 4 ul of the diluted samples were added to 100 ul of Renilla Luciferase Assay Solution in a luminometer tube, the tube was vortexed and light production was measured using a Turner TD 20/20 luminometer. The following readings were obtained:

| Solution | Sample          | RLU unbound | RLU Elution #1 |
|----------|-----------------|-------------|----------------|
| TP2      | Tergitol NP7    | 991.4       | 3981           |
|          |                 | 1189        | 3712           |
| TP3      | Tergitol NP9    | 867.7       | 3010           |
|          |                 | 830.9       | 2790           |
| TP4      | Tergitol NP10   | 921.6       | 4241           |
|          |                 | 896.6       | 3430           |
| TP7      | Tergitol 15-S-12| 1546        | 2731           |
|          |                 | 1596        | 2880           |
| TOP-1    | Tomah 18-15     | 884.9       | 3729           |
|          |                 | 1014        | 3682           |
| TOP-2    | Tomah 18-5      | 3243        | 1234           |
|          |                 | 3196        | 1187           |

Figure 6:
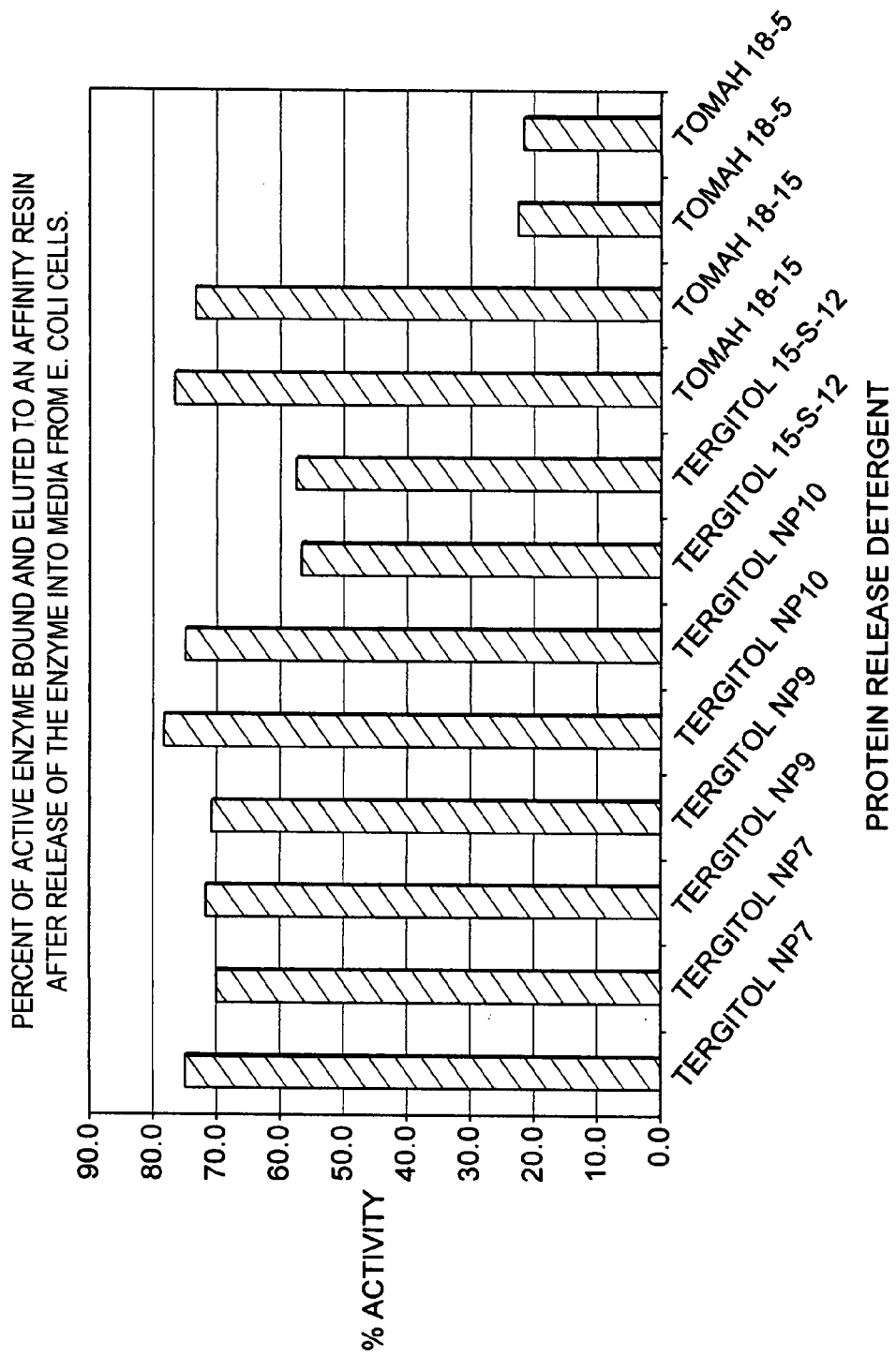
FIG. 6 is a bar graph that illustrates the percent of active enzyme bound and eluted to an affinity resin after release of the enzyme into media from E. coli cells as described in Example 11.

A calculation was performed to determine what percent of the active enzyme in the unbound sample and first eluted sample was present in the first eluted sample. These results are presented graphically in FIG. 6.

The results indicate that an enzyme could be released into the media and then captured and released from an affinity resin using the various detergents indicated, that span a select range of HLB values. These results also indicate that the lysis reagents of the present invention can be used in combination with automated systems that are useful for protein purification.

Example 12

Purification of Protein Released from *E. coli* on Non-magnetic Solid Supports

In this example, a variety of different properties of the materials that are the basis of this application will be demonstrated: the ability of the materials to be used with resins in a column format will be demonstrated as well as the ability of the protein release reagent to release protein from an older, stored culture if given additional time to perform.

(a) Preparation of Cell Lysate

Approximately 800 milliliters of *E. coli* culture was grown essentially as described in Example 5 with the alteration that dilution of the overnight culture was made into a much larger volume of L Broth+Tet [ratio of components kept constant]. After 6 hours of growth post IPTG addition, the culture was placed at 4C for 18 hours prior to use.

A dilution reagent was prepared by mixing 5 ml of 1M HEPES pH 7.5, 1 ml of 20% Triton X-100 solution [as prepared in Example 3] and 46 ml of nanopure water.

After storage at 4C, the cells were resuspended in the media by swirling the flask and the culture was allowed to warm to room temperature. After reaching room temperature, two 1.5 ml tubes were labeled 'treated' and 'untreated'. One ml of the resuspended culture was placed in the untreated tube.

A 10× Cell Lysis Reagent was prepared by mixing 4 g of Tomah E-18-15, 4 g of Triton X-100 (Sigma T 9284, lot 118h02970) and 47.6 g of HEPES (Sigma Chemical Co. H4034, lot 108H54102) in a beaker and adding water to approximately 160 ml. The solution was stirred and then adjusted to pH 7.5 by the slow addition of solid NaOH (Fisher S 318-1, lot 975006). After achieving pH 7.5, 49 mg of Polymyxin B Sulfate (Sigma P1004, 22K2517, 8140 U/mg solid) was dissolved in the solution and the volume adjusted to 200 ml.

One hundred microliters of the 10× Cell Lysis Reagent was placed in the tube labeled treated along with 900 ul of the bacterial culture. The tube was mixed by inversion and the treated and untreated tubes were centrifuged at 12,000 RPM for 4 min at room temperature. The supernatants were transferred to fresh labeled tubes and the pellets were resuspended in 1 ml of dilution reagent. Ten microliters of the supernatants and resuspended cells were diluted into 190 ul of dilution reagent, 10 ul of the diluted materials was added to 190 ul of Luciferase Assay Reagent, (LAR) [Promega Corp, E1483, 15517301] in a luminometer tube, the tube was vortexed 1 sec and light production was measured using a Turner TD 20/20 luminometer. The following values were recorded.

|  | Relative Light Units | |
| --- | --- | --- |
| Sample | Cell Supernatant | Cell Pellet |
| Treated Sample | 1443 | 115.1 |
| Untreated Sample | 120.2 | 3.267 |

There are two factors to note about these readings. First, Luciferase activity is apparently increased if the cell culture is treated with cell lysis reagent of the present invention. More specifically, the total measurable amount of Relative Light Units (Supernate+Pellet) was 1588.1 and 123.467, respectively for the treated and untreated samples. This demonstrates about a 12 fold increase in measurable enzyme activity by the addition of cell lysis reagent of the present invention. Without being bound to any theory, this phenomenon may be attributable to providing the enzyme with better access to substrate by creating perforations and/or expanding pores in the cell membrane.

Second, if one looks only to the percentage of activity found in the supernatant of both treated and untreated samples, one may come to the incorrect conclusion that the addition of the cell lysis reagent lowered the percentage of released protein. This anomaly is due to the inability to effectively measure the enzyme activity in the cell pellet in the untreated sample. In order to overcome this problem in effectively measuring enzyme activity in cell pellets, the pellets can be resuspended in 1× cell lysis reagent.

(b) Measurement of Enzyme Release Over Extended Reaction Time With Detergents

As many researchers will put cell cultures aside for extended periods of time, further study was performed to determine if additional enzyme could be released from older cell cultures (in other words, cell cultures were at least 18 hours old) by increasing the treatment time with the cell lysis reagent. Ninety one milliliters of the aforementioned cell culture (now approximately 36 hours old) was placed in a beaker, 1 ml removed to a 1.5 ml tube labeled "Pre" and 10 ml of 10× Cell Lysis Reagent added to the beaker and the beaker swirled for approximately one minute and then a 1 ml sample removed and placed in a 1.5 ml plastic microcentrifuge tube labeled "INIT". The Pre and INIT tubes were spun at 12,000 RPM for 4 minutes at room temperature and the supernatants removed to freshly labeled tubes. The pellets were resuspended in 1 ml of dilution reagent. The culture and Cell Lysis Reagent mixture was sampled at 5, 10, 20, and 120 minutes after addition of the Cell Lysis Reagent by removing a 1 ml sample, placing it in a 1.5 ml microfuge tube, spinning the tube at 12,000 RPM for 4 minutes at room temperature removing the supernates to fresh labeled tubes and resuspending the pellets in 1 ml of dilution reagent. Ten microliters of the supernates and resuspended cell pellets were diluted into 190 ul of dilution reagent, the solution was mixed by vortex treatment 1 sec, a 10 ul sample of the resulting mixture was then added to 100 ul of LAR in a luminometer tube, the tube mixed by 1 second vortex treatment and the light produced read immediately using a Turner TD 20/20 luminometer. The following readings were recorded:

|  | Relative Light Units | |
| --- | --- | --- |
| Sample | Cell Supernate | Cell Pellet |
| Pre | 14.01 | 345.1 |
| INIT | 1169 | 1437 |
| 5 min | 3050 | 1146 |
| 10 min | 4036 | 852.5 |
| 20 min | 4951 | 437.9 |
| 120 min | 5297 | 134.7 |

These results indicate that the cell lysis reagent of the present invention can release essentially all of the activity of the Luciferase expressed in an older culture if it is allowed to incubate with the culture for a period of time.

(c) Capture and Elution of Active Enzyme Using a Column-based System

In this section, a demonstration is presented that the protein solution resulting from direct application of a Cell Lysis Reagent solution to a column of resin can be used for reversibly binding and eluting an enzyme.

Purification of active enzymes is commonly accomplished by applying a solution of proteins containing the enzyme to a column containing a resin that reversibly binds and elutes the enzyme of interest under conditions where few other proteins bind and elute from the resin. However, commonly the applied protein lysate is generated by isolating cells from culture media, lysing these cells, often by physical means such as through the use of a French Press, removal of the cell debris and then applying the protein solution to a column of resin.

Two and one half ml of settled, nickel charged silica resin prepared in accordance with U.S. patent application No. 60/419,614, filed Oct. 18, 2002, entitled "Compositions and Methods of Separating Molecules", which is incorporated by reference in its entirety, was placed in a column and a second 2.5 ml of resin placed in a 50 ml closable tube. Eight 1.5 ml samples of the His-PPE-Luciferase bacterial culture-/Cell Lysis Reagent mixture was applied and fractions were collected. During the $8^{th}$ application, it was noted that the flow of liquid through the column had slowed substantially.

When the resin in the sample being tested was resuspended, the flow rate through the column was restored. The column was then washed with 4 ml of 10 mM imidazole in 100 mM HEPES, pH 7.5 and 1 ml fractions collected. The column was then eluted with multiple 1 ml samples of 500 mM imidazole in 100 mM HEPES, pH 7.5 and 1 ml fractions collected. The fractions collected during the application of the culture-Cell Lysis Reagent mixture were diluted 1:25 into dilution reagent, those collected during the wash and elution, 1:20. Ten microliter samples of the diluted fractions collected during the application of the Cell Lysis Reagent mixture and the wash fractions were added to 100 ul of LAR in a luminometer tube, the tube mixed by vortex 1 sec and light production measured immediately using a Turner TD 20/20 luminometer; 2 ul samples of the diluted fractions collected during the elution were added to 100 ul of LAR in a luminometer tube, the tube mixed by vortex for one second and light production measured immediately using a Turner TD 20/20 luminometer. The following readings were recorded:

| Sample | RLU |
| --- | --- |
| Load 1 | 25.48 |
| Load 2 | 45.15 |
| Load 3 | 61.20 |
| Load 4 | 79.68 |
| Load 5 | 84.26 |
| Load 6 | 74.60 |
| Load 7 | 87.10 |
| Load 8 | 66.87 |
| Wash 1 | 136.30 |
| Wash 2 | 12.82 |
| Wash 3 | 0.85 |
| Wash 4 | 0.29 |
| Elution #1 | 0.152 |
| Elution #2 | 10.26 |
| Elution #3 | 2001 |
| Elution #4 | 3088 |
| Elution #5 | 2150 |
| Elution #6 | 1050 |

These results indicate that the active enzyme was captured to a high degree and eluted from the resin using the inventive reagents and method. In fact, based upon the activity seen in previously described supernatant experiments a high percentage of the potential enzyme in the original culture was captured and eluted using the inventive method.

(d) Batch capture of Protein Released into Media for the Isolation of an Enzyme of Interest.

As shown in the preceding Section (c), direct application of a cell lysis reagent solution to a resin can be used to isolate an enzyme of interest. However, this method risks having the column become clogged with cells and cellular debris, requiring resuspension of the resin particles in the column to reestablish column flow. This clogging effect could be avoided if resin could be directly added to a cell lysis reagent mixture under conditions where the enzyme of interest would bind to the resin and the cells and cell debris decanted off the resin. In addition, if the resin could be rinsed in bulk before it was placed in a column, one could envision a very rapid method for the purification of an enzyme of interest: forming a cell lysis reagent mixture, directly applying resin particles to this mixture under conditions where the enzyme of interest binds to the resin while most other proteins remain unbound, optionally, washing the resin to remove traces of unbound protein present in the solution between the resin particles, and eluting the protein from the resin. In this Section, such a purification method is described.

Twenty milliliters of Cell Lysis Reagent mixture was placed in a fifty ml plastic capped tube that contained 2.5 ml of chelating silica resin charged with nickel prepared in accordance with U.S. patent application No. 60/419,614, filed Oct. 18, 2002, entitled "Compositions and Methods of Separating Molecules" (Atty docket no. B0174893). Immediately after resin addition, 10 ul of the solution was removed in placed in another tube taking care that resin particles were not removed from the fifty ml plastic tube. The tube was closed and mixed by slow inversion and additional 10 ul samples were taken at 2, 4, 6, 8, 10, 20 and 30 minutes post-resin addition. The resin was allowed to settle, the supernatant poured off and the resin was washed twice by: resuspending the resin in 2 aliquots of 5 ml of 10 mM imidazole in 100 mM HEPES pH 7.5, mixing the contents by slow inversion for 5 min, and pouring off the supernatant.

The resin was resuspended a third time in 5 ml of 10 mM imidazole, 100 mM HEPES pH 7.5 and then transferred to a column and the liquid allowed to drain from the settled resin until the liquid level just reached to level of the resin in the column. The liquid that eluted during this time was saved for later assay. Two 5 ml samples of 10 mM imidazole, 100 mM HEPES pH 7.5 were added to the column, and the eluted liquid collected for later use. An elution solution of 500 mM imidazole in 100 mM HEPES pH7.5 was then applied to the column and 1 ml samples of the eluted liquid were collected.

After several fractions were collected during the application of elution solution, 10 ul samples of the various fractions were diluted into 190 ul of dilution reagent. Ten aliquots of the diluted samples were added to 100 ul of LAR in a luminometer tube, the tube mixed by vortex 1 sec and light production was measured using a Turner TD 20/20 luminometer. As well 2 ul aliquots of the undiluted elution fractions were added to 100 ul of LAR in a luminometer tube, the tube mixed by vortex 1 sec, and light production measured using a Turner TD 20/20 luminometer. The following readings were recorded.

Samples taken during resin capture of enzyme from the Cell Lysis Reagent solution.

| Time post Resin addition | Relative Light Units |
| --- | --- |
| 0 [resin added] | 3992 |
| 2 | 2137 |
| 4 | 1356 |
| 6 | 1321 |
| 8 | 856.6 |
| 10 | 631.8 |
| 20 | 426.8 |
| 30 | 457.3 |

Samples taken during the washing of the resin post enzyme capture.

| Wash | RLU |
| --- | --- |
| #1 | 43,000 |
| #2 | 9,520 |

-continued

| Wash | RLU |
|---|---|
| #3 | 0.623 |
| #4 | 0.143 |

Samples of the fractions collected.

| Elute sample | RLU |
|---|---|
| 1 | 0.093 |
| 2 | 119.4 |
| 3 | 2264 |
| 4 | 5190 |
| 5 | 1815 |
| 6 | 982 |

These data demonstrate that an enzyme released into an *E. coli* cell culture by use of the described Cell Lysis Reagent can be captured directly in that solution and that the resin can be washed and enzyme subsequently released.

Example 13

High Throughput Functional Assay

In this example, an experiment was performed to demonstrate that a less than 1× final concentration of the cell lysis reagent of the present invention is still capable of cell lysis without the need for any mechanical pre-processing of the bacterial culture. This example demonstrates that recombinant proteins can be released from bacterial culture and analyzed in high throughput functional assays using less than 1× final concentration of the cell lysis reagent of the present invention.

A Ribonuclease inhibitor gene from Rat liver cDNA (OriGene Technologies, Inc., Rockville, Md.) was amplified by PCR and cloned into a vector according to conventional methods. See Maniatis et al., "Molecular Cloning: A Laboratory Manual," 2$^{nd}$ Edition, Cold Spring Harbor Laboratory, Cold Spring Harbor, N.Y. (1982). The vector was transformed into JM109 and CA7 *E. coli* strains and 200 ul aliquots of the transformation reactions were dispensed into 96 well plates (Falcon 96 well Micro Test III, Tissue Culture Plate with lid; catalog no. 3075). The transformed bacterial cells were grown overnight at 12C to allow for expression of the cloned ribonuclease inhibitor gene. Thereafter, 10 ul of the 1× cell lysis reagent described in Example 1 was added into each 200 ul culture contained in the well and the plate was gently shaken for 20 min. at RT using a Thermolyne Maxi-Mix III, Type 65800 (Model# M65825, Thermolyne, Dubuque, Iowa). The cell debris was removed from the wells by centrifuging the 96 well plates in a swinging bucket centrifuge (Beckman GS-6R Centrifuge, Beckman coulter, Fullerton, Calif.) for 15 minutes at 3000 rpm 10 ul aliquots of the supernatants from each well were analyzed for RNAse inhibition activity using a RNAse Detection Assay.

The RNAse Detection Assay is a modification of an existing agar plate based assay (Promega Corp., Part# AB150). Briefly, the pH of the solution changes as the RNA is hydrolyzed by RNAse, which is detected by an absorbance change at A650. Activity is determined as a total change in absorbance. Ribonuclease inhibitor activity is measured in this detection assay by inactivity of RNAse, or absence of a change in absorbance. Samples (such as purified clones or lysates) are compared to a positive control of wild type Ribonuclease inhibitor at amounts that are able to inhibit the amount of added RNAse, and also to a negative control sample of RNAse without inhibitor (negative for the absence of inhibition). The changes in measured absorbance are compared to controls for relative activity.

Materials:
Toluidine Blue 0 [Sigma T-3260]
Yeast Total RNA [Boehringer-Mannheim/Roche 109-223]
2M Tris-HCl Buffer, pH 7.3 [Promega LSS1472]
2M Tris-HCl Buffer, pH 8.0 [Promega LSS4227]
80% Glycerol [Promega LSS6208]
RNAseA [Sigma R-4642]

96 well microtiter plate, Immulon, flat bottom, polystyrene [Dynex, 3455]

Assay Solution:

200 mM Tris-HCl, pH 7.3, 2 mg/mL Total Yeast RNA, 0.0075% final v/v Toluidine Blue-0 (a 0.5% w/v stock was made in nanopure water, and 1.5% v/v is added to the solution). Solution was stored at 4C.

Procedure:
Samples were aliquoted to wells of a 96 well microtiter plate and 100 ul of assay solution was added per sample well. Solution and samples were mixed, and sample absorbance was measured at A650 at time=0. Plates were incubated at 37C for 30 minutes, and sample absorbance at A650 at time=30. Absorbance was measured by a Lucyl microplate luminometer with a photometeric filter capable of measuring absorbance at 650 nm [Anthos Labtec Instruments, Wals/Salzburg, Austria Model No.16-800]. The total absorbance change between time points was calculated and plotted. Data can be analyzed by comparing the change of absorbance of controls to that of experimental samples, or by comparing the ratios of the change in ribonuclease inhibitor sample absorbance change in RNAseA sample absorbance to the ratios of change in-experimental sample absorbance: change in RNAseA sample absorbance.

Control experiments were performed for the RNAse Detection Assays. The positive control for inhibition activity consisted of combining 10 ul of RNAse dilution buffer (10 mM Tris-HCl, pH 8.0, 5% glycerol) with RNAseA to a final concentration of 1 ng/ul. 10 ul (approximately 20 U) of purified Rat Ribonuclease inhibitor was added to the reaction and allowed to interact for about 1-2 minutes. The negative control for inhibition followed the same protocol for the positive control, exhibit no Rat Ribonuclease inhibitor was added. Additionally, a negative control of buffer alone with no enzymes was utilized. Absorbance was measured for all samples. See FIGS. 10 and 11. These results demonstrate that one could use the cell lysis reagent of the present invention for the direct lysis of bacterial cells without centrifugation. This approach is useful for studying downstream high throughput protein functional assays.

Example 14

High Throughput Purification of Different Recombinant Proteins

In this Example, the cell lysis buffer of the described invention was used for the high throughput purification of several different polyhistidine tagged proteins; ribonuclease inhibitor, RNaseHI, methionyl tRNA synthetase, thermostable firefly luciferase, β-galactosidase, MGH, and humanized Renilla luciferase. Purification of these His-tagged proteins from bacterial cells was performed using a kit for the affinity purification of histidine tagged proteins. MagneHis™ Protein Purification System (Promega Corporation, Cat# V8500). The kit includes nickel attached magnetic particles, binding/washing buffer (100 mM HEPES buffer pH 7.5 and 10 mM imidazole), elution buffer (100 mM HEPES buffer pH 7.5 and 500 mM imidazole) and the bacterial cell lysis reagent of the invention as described in Example 1.

Bacterial cells capable of expressing various his-tagged proteins were grown to OD600 0.4-0.6 and protein expression was induced by the addition of IPTG to a final concentration of 1 mM. Cells were grown for three more hours and 1 ml of each culture was aliquoted into 96-well plates. Cells were pelleted by centrifugation and the culture medium was removed. Thereafter, 200 ul of cell lysis reagent was added to each pellet, the pellet was resuspended, the mixture was incubated while shaking for 10 minutes, and the plates were placed on a Beckman Biomek 2000 for further purification. The resultant lysate was added directly to the MagneHis™ particles (30 ul) in 100 ul aliquots. Next, the particles with bound proteins were treated with the washing/binding buffer. Proteins were subsequently eluted with buffer containing 0.5M imidazole. The elution samples were then analyzed by SDS-PAGE.

Figure 7:
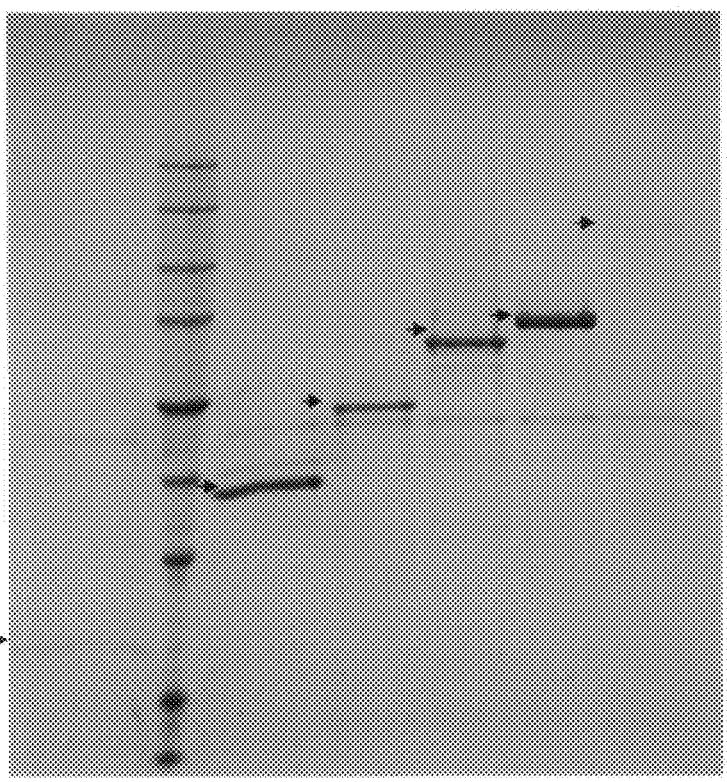
FIG. 7 is a photograph of a SDS-PAGE gel showing the relative degree of purification of multiple proteins in a robot using a cell lysis reagent as described in Example 14. Arrows indicate corresponding proteins. Lane 1: His-RNaseHI; lane 2: His-humanized Renilla luciferase; lane 3: His-RNasin; lane 4: His-thermostable firefly luciferase; lane 5: His-MGH; lane 6: His-beta galactosidase; M: Molecular weight markers.

The results are shown in FIG. 7 Lane numbers at the top of the figure correspond to the purified His-tagged proteins indicated by arrows in each lane; M=molecular weight markers, 1=His-RNase HI, 2=His-humanize Renilla luciferase, 3=His-RNasin, 4=His-thermostable firefly luciferase, 5=His-MGH, 6=His-β-galactosidase. These results show the applicability of the cell lysis reagent of the present invention in purifying multiple His-tagged proteins on a robotics platform.

Example 15

Purification of Proteins from the Lysed Cells Without Centrifugation

In this example, E. coli JM109 cells capable of expressing his-methionyl tRNA synthetase was used. Cells were grown and induced as described in Example 14. After induction, 1 ml of cells was aliquoted into each of two different tubes, the samples were centrifuged, and the cell pellets were recovered. 200 ul aliquots of the cell lysis reagent were added to each of the pellets and the mixture was incubated for 10 min at room temperature. After lyses, one of the samples was centrifuged to remove cell debris and other contaminants. This tube was labeled "centrifuged sample". The other sample was processed without any centrifugation. This sample was labeled as "non-centrifuged sample".

Figure 8:
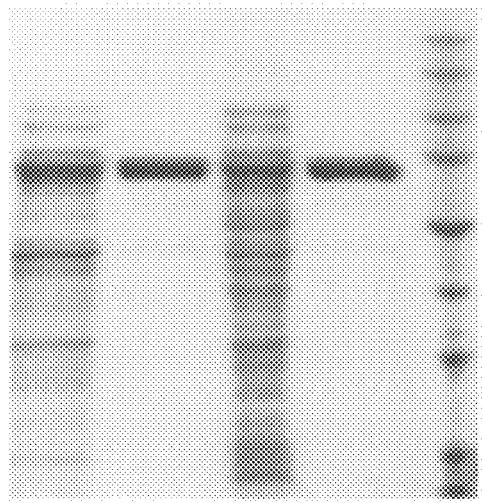
FIG. 8 is a photograph of a SDS-PAGE gel showing the relative degree of purity of proteins from centrifuged versus non-centrifuged cells as described in Example 15. Lane 1: centrifuged lysate 5 ul of sample; lane 2: purified protein from centrifuged lysate 20 ul of sample; lane 3: non-centrifuged lysate 5 ul of sample; lane 4: purified protein from non centrifuged lysate. 20 ul of sample; lane 5: molecular weight markers.

MagneHis™ purification particles (30 ul) (MagneHis™ Protein Purification System, Promega Corporation, Cat# V8500) were added directly to both samples and the mixture was thoroughly mixed. The particles were washed with binding buffer, and the proteins were eluted with binding buffer containing 0.5M imidazole. These samples were then analyzed by SDS-PAGE. The results are shown in FIG. 8. Lane numbers 1 thru 4 corresponds to experimental samples; 1) 5 ul of centrifuged crude lysate, 2) 20 ul of purified protein from centrifuges lysate, 3) 5 ul sample of non-centrifuged crude lysate, 4) 20 ul of purified protein from non-centrifuged lysate. Lane 5 contains a molecular weight marker.

These results indicate that (1) the cell lysis reagent of the present invention could be used for the purification of recombinant proteins on various robotic platforms and (2) the proteins could be uniformly purified from each well of the 96-well plate using the inventive method described herein.

Example 16

Automated Purification of Proteins from the Lysed Cells in Multiple Platforms

In this example, recombinant proteins expressed in a bacterial cell culture were purified in a multi-well format for high throughput applications for protein purification using the inventive method. Three robotic platforms were evaluated for high throughput protein purification; the Beckman FX, Beckman Biomek 2000, and the Tecan Genesis RSP.

Bacterial cells capable of expressing his-tagged thermostable firefly luciferase prepared as described in Example 5 were grown to OD600 0.4-0.6 and protein expression was induced by addition of IPTG to a final concentration of 1 mM. Cells were grown for three more hours and 1 ml of the culture was aliquoted into all wells of 96-well plates. Cells were pelleted by centrifugation and the culture media was removed. Thereafter, 200 ul of the 1× Cell Lysis Reagent described in Example 1 was aliquoted into each of the wells of a 96 deep well plate. The pellet/reagent was mixed by pipetting each well 10 times and the plate was agitated for 5 minutes on an orbital shaker. 100 ul aliquots of the lysate were removed from each well and transferred to a second plate containing 30 ul of MagneHis™ Purification particles. The lysate and particles were initially mixed via pipette and further mixed on an orbital shaker for 1 minute. The plate was placed on a MagnaBot® magnetic device [Promega Corporation, Part# V8151] for 1 minute.

The liquid flow through (waste) was removed. via robotic manipulation using a predefined computerized program for each of the three robotic platforms. Another 100 ul of lysate was added to each of the wells. The lysate and particles were mixed via pipette and further mixed on an orbital shaker for 1 minute. The plate was again placed on the MagnaBot® magnetic device for 1 minute. The liquid flow-through was removed. and the particles were washed using 100 ul of the wash/binding buffer (100 mM HEPES and 10 mM imidazole). The particles were shaken for 3 minutes and the plate was placed on the MagnaBot® device for 1 minute. The Wash/binding buffer was removed. 100 ul wash/binding buffer was added and the process repeated two more times. The particles and buffer were then resuspended by pipetting and shaking for 1 minute.

Following the sample manipulation, the 96 well plate was placed on the MagnaBot® magnetic device for 1 minute and 200 ul of elution buffer [100 mM HEPES (pH 7.5), 500 mM imidazole)] was added. Eluted proteins were transferred to a separate plate for analysis. Samples were analyzed by SDS-PAGE (See FIG. 9).

These results indicate that (1) the cell lysis reagent of the present invention could be used for the purification of recombinant proteins on various robotic platforms and (2) the proteins could be uniformly purified from each well of the 96-well plate using the inventive method described herein.

Example 17

Release of Protein from E. coli Cells Using a Second Cell Permibilization Reagent Octyl-beta-thioglucopyranoside In this Example, various reagent formulations are compared for their ability to release protein from E. coli cells. These formulations use two different chemical reagents, polymyxin B or Octyl beta thioglucopyranoside, that are known to permibilize E. coli cells alone and in combination with each other and with detergents that can stabilize protein activity [Triton X 100 and Toman E-18-15].

The following solutions were assembled.
PRS#1 2% Tomah E-18-15, 2% Triton X100, 100 U/ml polymyxin B, 500 mM HEPES, pH 7.5
PRS#2 As described for PRS #1 but also containing 6% w/v octyl beta thioglucopyranoside
PRS#3 10% Triton X100, 3% Tomah E-18-15, 10 mM Imidazole, 500 mM HEPES pH 7.5, 6% octyl beta thioglucopyranoside.
PRS#4 As PRS#3 but without Tomah E-18-15
PRS#5 2% Tomah E-18-15, 2% Triton X 100, 500 mM HEPES, pH 7.5, 100 mM Imidazole, 6% w/v octyl beta thioglucopyranoside
PRS #6 As PRS#5 but without 6% w/v octyl beta thioglucopyranoside A culture expressing a his-tagged thermostable luciferase from Photinus pennsylvanica prepared as described in Example 5 was grown in Luria Broth also containing 100 ug/ml ampicillin overnight at 37C with shaking. One ml seed stocks were prepared and stored at −70C. The day of the experiment one ml of seed stock is used to inoculate 50 ml of Luria Broth containing 100 ug/ml ampicillin and the culture is grown at 25C with shaking until an OD600 of 0.4 to 0.6 is achieved. At that point, 1M IPTG (isopropyl-β-D-thiogalactopyranoside Promega catalog# V3951) is added to the culture a final concentration of 1 mM and the culture is allowed to grow overnight at room temperature with shaking.

The next day, duplicate 100 ul samples of PRS#1-#6 were placed in labeled 1.5 ml tubes. Nine hundred microliters of the overnight culture was then added to the 1.5 ml tubes and the tubes were mixed by inversion for ten minutes at room temperature.

After the 10 minutes of inversion, 200 ul samples of the tubes were spun in separate tubes for 15 minutes full speed in a microfuge at 4C to pellet any intact cells and cell debris. After spinning, the supernate was carefully removed to fresh, labeled tubes.

Ten microliters of the remaining unspun treated cell sample and the supernate samples were diluted into 990 ul of 1× Cell Lysis Reagent (25 mM Tris-phosphate pH 7.8, 2 mM dithiothreitol, 2 mM 1,2 diamino cyclohexane-N,N,N, N-tetraacetic acid, 10% glycerol, 1% Triton x-100 containing 1 mg/ml BSA (bovine serum albumin) and the diluted solutions were kept on ice. One hundred microliter samples of luciferase assay reagent (LAR) (1.07 mM magnesium carbonate, 0.1 mM EDTA, 2.67 mM magnesium sulfate, 33.3 mM dithiothreitol, 0.27 mM coenzyme A, 0.53 mM ATP and 0.47 mM luciferin) was placed in Turner luminometer tubes. Five microliters of the diluted samples are added to one of the luminometer tubes containing LAR, the tube mixed for 1-2 sec then the light produced by the reaction was read using a Turner TD 20/20 luminometer. The following values were recorded.

| Release reagent | Sample | Light Units | % Enzyme in Supernate |
|---|---|---|---|
| PRS #1 | Total Lysate | 3249 | |
| | Supernate | 169.2 | 5.21 |
| PRS #1 | Total Lysate | 3451 | |
| | Supernate | 233.7 | 6.77 |
| PRS #2 | Total Lysate | 5216 | |
| | Supernate | 4699 | 90.09 |
| PRS #2 | Total Lysate | 4799 | |
| | Supernate | 4782 | 99.65 |
| PRS #3 | Total Lysate | 3778 | |
| | Supernate | 1246 | 32.98 |
| PRS #3 | Total Lysate | 3453 | |
| | Supernate | 1070 | 30.99 |
| PRS #4 | Total Lysate | 4140 | |
| | Supernate | 1533 | 37.03 |
| PRS #4 | Total Lysate | 4049 | |
| | Supernate | 1835 | 45.32 |
| PRS #5 | Total Lysate | 4979 | |
| | Supernate | 4740 | 95.20 |
| PRS #5 | Total Lysate | 5388 | |
| | Supernate | 4380 | 81.29 |
| PRS #6 | Total Lysate | 3295 | |
| | Supernate | 191.4 | 5.81 |
| PRS #6 | Total Lysate | 3271 | |
| | Supernate | 63.76 | 1.95 |

These data demonstrate that protein stabilizing detergents can be used with a variety of cell permebilization reagents to create a solution that can effectively allow protein to be released from E. coli cells into media. Release of protein was confirmed by SDS PAGE analysis of the supernates and total lysate.

Example 18

Addition of Protein Stabilization Detergents to Solutions of Octyl Beta Thioglucopyranoside Can Produce a Solution that is Not as Damaging to Protein Activity as Solutions Not Containing the Stabilizing Chemicals In this Example, solutions of octyl beta thioglucopyranoside in the presence and absence of protein stabilizing detergents will be incubated with firefly luciferase. The solutions containing the stabilizing detergents will be shown to retain significantly more enzyme activity than solutions of octyl beta thioglucopyranoside not containing the detergents.

The following solutions were assembled:

| | |
|---|---|
| Test Solution #1 | 6% Octyl beta thioglucopyranoside in 500 mM HEPES pH 7.5 |
| Test Solution #2 | As Test Solution #1 but also contains 10% v/v Triton X100 |
| Test Solution #3 | As PRS #3 in Example 17 above |
| Test Solution #4 | 6% Octyl beta thioglucopyranoside, 2% Triton X100 (v/v), 2% TOMAH E-18-15 (vol/vol) in 500 mM HEPES pH 7.5 |

Forty microliters of the test solutions above were diluted with 360 ul of deionized water 1:10 into duplicate tubes. One final set of tubes containing 1× Cell Lysis Reagent (25 mM Tris-phosphate pH 7.8, 2 mM dithiothreitol, 2 mM 1,2 diamino cyclohexane-N,N,N,N-tetraacetic acid, 10% glycerol, 1% Triton x-100)-containing 1 mg/ml BSA (bovine serum albumin Promega catalog# W3841) also containing 1 mg/ml in BSA was placed into duplicate tubes. One set of tubes was placed on ice, the other allow to remain at room temperature. A solution containing wild-type luciferase from *Photinus pyralis* (4 ul of a 25 mM Tris acetate pH 7.5, 1 mMEDTA, 1 mM DTT, 0.2M ammonium sulfate, 15% glycerol, 30% ethylene glycol, 14.6 ug luciferase/ul; solution is stored at −70C prior to use) was added to all tubes and incubated on ice or at room temperature for 20 min. After the 20 min incubation, the solutions were all diluted 1/100 into 1× Cell Lysis Reagent reagent also 1 mg/ml in BSA.

One hundred microliter samples of Luciferase Assay Reagent described in Example 16 was placed in Turner Luminometer tubes. Ten microliter samples of the diluted enzyme stocks in CCLR with BSA were added, the tubes were mixed and the light read using a Turner TD 20/20 Luminometer. Duplicate light readings were performed on each sample. The following values were obtained

|                       | Incubation temperature |        |                    |        |
|-----------------------|-----------|--------|---------|---------|
| Solution              | On ice    |        | at room temperature |        |
| Test Solution #1      | 811.6     | 842.8  | 0.072   | 0.15    |
| Test Solution #2      | 2901      | 2885   | 716.9   | 762.9   |
| Test Solution #3      | 3237      | 3251   | 1639    | 1672    |
| Test Solution #4      | 3007      | 3031   | 112.3   | 123     |
| CCLR dilution control | 4625      | 4692   | nd      | nd      |

These data demonstrate that the addition of the protein stabilization reagents greatly improved the stability of the luciferase enzyme in the presence of the Octyl beta Thioglucopyranoside. These data combined with those of previous Example 17 that demonstrated that the addition of these materials did not prevent the release of protein from *E. coli* cells by cell protein release reagents, do demonstrate that the combination of these reagents results in an improved protein release material than use of the protein release reagent alone as the combination helps retain the activity of proteins that can be harmed by the release reagent.

While the present invention has been described and exemplified with some specificity, those skilled in the art will appreciate the various modifications, including variations, additions and omissions that may be made in what has been disclosed herein without departing from the spirit of the invention. Accordingly, it is intended that these modifications also be encompassed by the present invention and that the scope of the present invention be limited solely by the broadest interpretation that lawfully can be accorded the appended claims. All references cited herein are incorporated by reference in their entirety.

What we claim:

1. A composition comprising 2% Tomali E-18-15, 2% Triton X100, and 6% octyl beta thioglucopyranoside in 500 mM HEPES (pH 7.5).

* * * * *